US009198924B2

(12) United States Patent
Mates et al.

(10) Patent No.: US 9,198,924 B2
(45) Date of Patent: Dec. 1, 2015

(54) ORGANIC COMPOUNDS

(75) Inventors: Sharon Mates, New York, NY (US); Allen A. Fienberg, New York, NY (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 187 days.

(21) Appl. No.: 12/514,712

(22) PCT Filed: Nov. 13, 2007

(86) PCT No.: PCT/US2007/023854
§ 371 (c)(1),
(2), (4) Date: May 13, 2009

(87) PCT Pub. No.: WO2008/063505
PCT Pub. Date: May 29, 2008

(65) Prior Publication Data
US 2010/0087450 A1    Apr. 8, 2010

Related U.S. Application Data

(60) Provisional application No. 60/858,732, filed on Nov. 13, 2006, provisional application No. 60/873,175, filed on Dec. 5, 2006.

(51) Int. Cl.
*A61K 31/519* (2006.01)
*A61K 31/52* (2006.01)
*A61K 45/06* (2006.01)
*A61K 31/70* (2006.01)
*A61K 31/00* (2006.01)
*A61K 31/165* (2006.01)
*A61K 31/19* (2006.01)

(52) U.S. Cl.
CPC .................. *A61K 31/70* (2013.01); *A61K 31/00* (2013.01); *A61K 31/165* (2013.01); *A61K 31/19* (2013.01); *A61K 31/519* (2013.01); *A61K 31/52* (2013.01); *A61K 45/06* (2013.01)

(58) Field of Classification Search
CPC ..... A61K 31/70; A61K 31/00; A61K 31/165; A61K 31/19; A61K 31/519; A61K 31/52; A61K 45/06
See application file for complete search history.

(56) References Cited

U.S. PATENT DOCUMENTS

| 4,666,908 A | 5/1987 | Hamilton |
| 4,738,985 A | 4/1988 | Kluger et al. |
| 5,294,612 A | 3/1994 | Bacon et al. |
| 5,393,755 A | 2/1995 | Neustadt et al. |
| 5,719,283 A | 2/1998 | Bell et al. |
| 5,824,683 A | 10/1998 | McKittrick et al. |
| 5,849,770 A | 12/1998 | Head et al. |
| 5,939,419 A | 8/1999 | Tulshian et al. |
| 5,962,492 A | 10/1999 | Warrellow et al. |
| 6,013,621 A | 1/2000 | Nishi et al. |
| 6,133,273 A | 10/2000 | Gilbert et al. |
| 6,235,742 B1 | 5/2001 | Bell et al. |
| 6,316,444 B1 | 11/2001 | Hunt et al. |
| 6,423,716 B1 | 7/2002 | Matsuno et al. |
| 6,492,371 B2 | 12/2002 | Roylance |
| 6,498,165 B1 | 12/2002 | Armstrong et al. |
| 6,552,029 B1 | 4/2003 | Davis et al. |
| 6,586,423 B2 | 7/2003 | Bilodeau et al. |
| 6,599,908 B1 | 7/2003 | Davis et al. |
| 6,649,608 B2 | 11/2003 | Pease et al. |
| 6,670,368 B1 | 12/2003 | Breault et al. |
| 6,693,099 B2 | 2/2004 | Degenhardt et al. |
| 6,756,373 B1 | 6/2004 | Allerton et al. |
| 6,969,719 B2 | 11/2005 | Asberom et al. |
| 7,153,824 B2 | 12/2006 | Palmer et al. |
| 7,320,785 B2 | 1/2008 | Greengard et al. |
| 8,273,750 B2 | 9/2012 | Li et al. |
| 8,273,751 B2 | 9/2012 | Li et al. |
| 8,536,159 B2 | 9/2013 | Li et al. |
| 2003/0069246 A1 | 4/2003 | Darrow et al. |
| 2003/0162782 A1 | 8/2003 | Grossman et al. |
| 2003/0211040 A1* | 11/2003 | Greengard et al. ............ 424/9.2 |
| 2004/0087517 A1 | 5/2004 | Burnet et al. |
| 2004/0259792 A1 | 12/2004 | Palmer et al. |
| 2008/0176961 A1 | 7/2008 | Greengard et al. |
| 2008/0188492 A1 | 8/2008 | Li et al. |
| 2008/0193964 A1 | 8/2008 | Greengard et al. |
| 2008/0194592 A1 | 8/2008 | Mates et al. |
| 2010/0087450 A1 | 4/2010 | Fienberg et al. |
| 2010/0173878 A1 | 7/2010 | Li et al. |
| 2010/0273753 A1 | 10/2010 | Li et al. |
| 2010/0323997 A1 | 12/2010 | Fienberg et al. |
| 2011/0237561 A1 | 9/2011 | Li et al. |
| 2011/0281832 A1 | 11/2011 | Li et al. |
| 2011/0312978 A1 | 12/2011 | Davis et al. |

(Continued)

FOREIGN PATENT DOCUMENTS

DE    199 31 206    1/2001
EP    0063381    4/1982

(Continued)

OTHER PUBLICATIONS

Zaharna et al. Expert opinion on pharmacotherapy of narcolepsy. Expert Opin. Pharmacother. (2010) 11(10): 1633-1645.*
Xia et al. Synthesis and Evaluation of Polycyclic Pyrazolo[3,4-d]pyrimidines as PDE1 and PDE5 cGMP Phosphodiesterase Inhibitors. J. Med. Chem. 1997, 40, 4372-4377.*
Ahn et al, *J Med Chem* (1997) 40:2196-2210.
Banker et al, *Modem Pharmaceutics*, Marcel Dekker, New York 1996.
Bender et al, *Pharmacol Rev* (2006) 58: 488-520.
Chebib et al, *Bioorg & Med Chem* (2000) 8:2581-2590.
Dewald et al, *J Med Chem* (1988) 31:454-461.
Fienberg et al, *Science* (1998) 281:838-842.
Greengard et al, *Neuron* (1999) 23:435-447.
Jiang et al, *J Org Chem* (2005) 70:2824-2827.
Mani et al, *Science* (2000) 287:1053.

(Continued)

*Primary Examiner* — Renee Claytor
(74) *Attorney, Agent, or Firm* — Hoxie & Associates LLC

(57) ABSTRACT

The present invention relates to a new use of phosphodiesterase 1 (PDE1) inhibitors for the treatment and/or prophylaxis of narcolepsy.

12 Claims, No Drawings

(56) References Cited

U.S. PATENT DOCUMENTS

| | | |
|---|---|---|
| 2012/0053190 A1 | 3/2012 | Fienberg et al. |
| 2012/0071450 A1 | 3/2012 | Li et al. |
| 2012/0094966 A1 | 4/2012 | Li et al. |
| 2012/0136013 A1 | 5/2012 | Li et al. |

FOREIGN PATENT DOCUMENTS

| | | |
|---|---|---|
| EP | 0201188 | 12/1986 |
| EP | 0911333 | 4/2002 |
| JP | 53031694 | 3/1978 |
| WO | WO 91/19717 | 12/1991 |
| WO | WO 94/19351 | 9/1994 |
| WO | WO 98/46606 | 10/1998 |
| WO | WO 98/52568 | 11/1998 |
| WO | WO 02/060428 | 8/2002 |
| WO | WO 03/002567 | 1/2003 |
| WO | WO 03/020702 | 3/2003 |
| WO | WO 03/020724 | 3/2003 |
| WO | WO 03/042216 | 5/2003 |
| WO | WO 03/057188 | 7/2003 |
| WO | WO 2004/056831 | 7/2004 |
| WO | WO 2006/133261 | 12/2006 |
| WO | WO 2007/025103 | 3/2007 |
| WO | WO 2007/143705 | 12/2007 |
| WO | WO 2009/073210 | 6/2009 |
| WO | WO 2009/075784 | 6/2009 |

OTHER PUBLICATIONS

Morissette et al, *Advanced Drug Delivery Reviews* (2004) 56:275-300.
Poulsen et al, *Bioorg & Med Chem Letter* (2001) 11:191-193.
Reed et al, *J Neurosci* (2002) 22(12):5188-5197.
Turko et al, *Mol Pharmacol* (1990) 56:124-130.
Vippagunta et al, *Advanced Drug Delivery Reviews* (2001) 48:3-26.
Wolff et al, *Burger's Medicinal Chemistry and Drug Discovery*, Fifth Ed., vol. 1: Principles and Practice, John Wiley & Sons (1995) p. 975.
Xia et al, *J Med Chem* (1997) 40:4372-4377.
Ahn, H., et al., "Potent Tetracyclic Guanine Inhibitors of PDE1 and PDE5 Cyclic Guanosine Monophosphate Phosphodiesterases with Oral Antihypertensive Activity", Journal of Medicinal Chemistry, vol. 40, No. 14, pp. 2196-2210, (1997).
Hublin, C., "Norcolepsy. Current Drug Treatment Options", CNS Drugs, Adis International, Auckland, NZ, vol. 5, No. 6 pp. 426-436, (Jan. 1, 1996).
Ribeiro, J. A., et al., "Caffeine and Adenosine", Journal of Alzheimer's Disease 2010 IOS Press NLD LNKD- DOI: 10.3233/JAD-2010-1379, vol. 20, No. SUPPL. 1, pp. S3-S15, (2010).
Sarkadi, A., et al., "Effect of Vinpocetine on the Sleep—Wake Cycle of Rats", Drug Development Research, New York, NY, U.S., vol. 14, No. 3-4, pp. 335-342, (Jan. 1, 1988).
Xia, Yan, et al., "Synthesis and Evaluation of Polycyclic Pyrazolo (3,4-d) Pyrimidines as PDE1 and PDE5 cGMP Phosphodiesterase Inhibitors", Journal of Medicinal Chemistry, vol. 40, No. 26, pp. 4372-4377, (Dec. 19, 1997).
Nishi, A., et al., "Advanced Research on Dopamine Signaling to Develop Drugs for the Treatment of Mental Disorders: Biochemical and Behavioral Profiles of Phosphodiesterase Inhibition in Dopaminergic Neurotransmission", J. Pharmacol. Sci. vol. 114, pp. 6-16, (2010).
U.S. Appl. No. 12/746,236, Final Rejection Mar. 27, 2012.
U.S. Appl. No. 12/746,236, Non-Final Office Action Nov. 29, 2011.
Vatter, et al., Differential Phosphodiesterase Expression and Cytosolic Ca2+ in Human CNS Tumour Cells and in Non-Malignant and Malignant Cells of Rat Origin, J. of Neurochemistry, 93, 321-329 (2005).
Dewald et al., Synthesis and Potential Antipsychotic Activity of 1 H-lmidazo[1.2-c]pyrazolo[3,4-e]pyrimidines, J. Med. Chem. 1988, 31, pp. 454-461.
Burnouf et al., "Synthesis, Structure-Activity Relationships, and Pharmacological Profile of 9-Amino-4-0xo-1-Phenyl-3,4,5,6, 7-Tetrahydrol[I,4]Diazepino[6, 7, 1-hi]lndoles: Discovery of Potent, Selective Phosphodiesterase Type 4 Inhibitors," (2000), J. Med. Chem., 43:4850-4867.
Polli et al., "Expression of a Calmodulin-Dependent Phosphodiesterase Isoform (PDE1 B1) Correlates With Brain Regions Having Extensive Dopaminergic Innervation," (1994), The Journal of Neuroscience, 14:1251-1261.
Han et al., "The Calcium/Calmodulin-dependent Phosphodiesterase PDE1C Downregulates Glucose-induced Insulin Secretion", J. Bio, Chem., 1999,274(32), pp. 22337-22344.
Murray et al., "Expression and activity of cAMP phosphodiesterase isoforms in pulmonary artery smooth muscle cells from patients with pulmonary hypertension: role for PDE1", Am. J. Physiol. Lunr:l Cell Mol. Physiol. 2007, 292, pp. L294-L303.
Rybalkin et al., "Cyclic GMP Phosphodiesterases and Regulation of Smooth Muscle Function", Circ. Res. 2003,93, pp. 280-291.
Shimizu et al., "Calmodulin-Dependent Cyclic Nucleotide Phosphodiesterase (PDE1) Is a Pharmacological Target of Differentiation-Inducing Factor-1, an Antitumor Agent Isolated from Dictyostelium", Cancer Research, 2004, 64, pp. 2568-2571.
Bastia et al., Effect of $A_1$ and $A_{2A}$ Adenosine Receptor Ligands in Mouse Acute Models of Pain, Neuroscience letters (2002) 328:241-244.
Lundqvist et al., Exploitation of Structural and Regulatory Diversity in Glutamate Racemases, Nature (2007) 447:817-822.
Murray et al., LY503430, a Novel __-Amlno-3-hydroxy-5-methylisoxazole-4-proplonlc Acid Receptor Potentiator with Functional, Neuroprotective and Neurotrophic Effects in Rodent Models of Parkinson's Disease JPEJ (2003) 306:752-762.
Porsolt et al. Nature (1977) 266:730-732.
Ungerstedt, Acta Physiology Second Suppl. (1971) 367:1-48.
Ungerstedt et al., Brain Research (1970) 24: 485-493.
Wennogle et al. XXVII CINP Congress (Abstract), "Cognitive Enhancement by Inhibition of Phosphodiesterase-1" (2010).
Burgess, C. R., et al., "Dopaminergic Regulation of Sleep and Cataplexy in a Murine Model of Narcolepsy", SLEEP, (2010), 33(10):1295-1304.
Ehrman et al., "Phosphodiesterase 1B differentially modulates the effects of methamphetamine on locomotor activity and spatial learning through DARPP32—dependent pathways: evidence from PDE1B-DARPP32 double-knockout mice", *Genes Brain Behav.* Oct. 2006; 5(7):540-551.

\* cited by examiner

ORGANIC COMPOUNDS

CROSS REFERENCE TO RELATED APPLICATIONS

This application is a U.S. filing under 35 U.S.C. 371 of PCT/US2007/023854 filed on Nov. 13, 2007, which claims the benefit of 60/858,732 filed on Nov. 13, 2006 and 60/873,175 filed on Dec. 5, 2006, the contents of each of which are incorporated herein by reference.

TECHNICAL FIELD

The present invention relates to a new use for compounds that inhibit phosphodiesterase 1 (PDE1), e.g., that inhibit PDE1-mediated suppression of the dopamine D1 receptor intracellular pathway, specifically for the treatment of narcolepsy.

BACKGROUND OF THE INVENTION

Narcolepsy is a chronic neurological disorder caused by the brain's inability to regulate sleep-wake cycles normally. At various times throughout the day, people with narcolepsy experience fleeting urges to sleep. If the urge becomes overwhelming, patients fall asleep for periods lasting from a few seconds to several minutes. In rare cases, some people may remain asleep for an hour or longer.

Narcoleptic sleep episodes can occur at any time, often without warning, and may be quite dangerous if patients are driving or operating machinery. In addition to daytime sleepiness, patients may experience cataplexy, or the sudden loss of voluntary muscle tone; vivid hallucinations during sleep onset or upon awakening; brief episodes of total paralysis at the beginning or end of sleep; and/or automatic behavior, such as talking or performing routine activities during a sleep episode but having no memory of these activities upon waking. Most patients also experience frequent awakenings during nighttime sleep. For these reasons, narcolepsy is considered to be a disorder of the normal boundaries between the sleeping and waking states.

Eleven families of phosphodiesterases (PDEs) have been identified but only PDEs in Family I, the $Ca^{2+}$-calmodulin-dependent phosphodiesterases (CaM-PDEs), have been shown to mediate the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyms, olfactory tract and cerebellum, and its expression correlates with brain regions having high levels of dopaminergic innervation. Although PDE1B is primarily expressed in the central nervous system, it may be detected in the heart. PDE1C is primarily expressed in olfactory epithelium, cerebellar granule cells, and striatum. PDE1C is also expressed in the heart and vascular smooth muscle.

Cyclic nucleotide phosphodiesterases downregulate intracellular cAMP and cGMP signaling by hydrolyzing these cyclic nucleotides to their respective inactive 5'-monophosphates (5'AMP and 5'GMP). CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase (CaMKII) and calcineurin and to activation of CaM-PDEs, resulting in reduced cAMP and cGMP. Dopamine D1 receptor activation, on the other hand, leads to activation of calcium dependent nucleotide cyclases, resulting in increased cAMP and cGMP. These cyclic nucleotides in turn activate protein kinase A (PKA; cAMP-dependent protein kinase) and/or protein kinase G (PKG; cGMP-dependent protein kinase) that phosphorylate downstream signal transduction pathway elements such as DARPP-32 (dopamine and cAMP-regulated phosphoprotein) and cAMP responsive element binding protein (CREB).

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) or endorphin intracellular signaling pathway. For example, inhibition of PDE1B may potentiate the effect of a dopamine D1 agonist by protecting cGMP and cAMP from degradation, and similarly inhibit dopamine D2 receptor signaling pathways, by inhibiting PDE1 activity. PDE1 inhibitors are therefore potentially useful in diseases characterized by reduced dopamine D1 receptor signaling activity. See generally, WO 03/020702.

EP 0201188 and EP 0911333, the contents of which are incorporated herein by reference, disclose certain 1,3,5,-substituted, 6,7-dihydro-1H-pyrazolo[4,3-d]pyrimidin-7-one compounds, claimed to be useful for treatment of cardiovascular disease, erectile dysfunction, and other disorders. These compounds are not, however, taught or suggested to be useful for the treatment of diseases involving disorders of the dopamine D1 receptor intracellular pathway, particularly diseases relating to sleep disorders such as narcolepsy. PCT/US2006/33179, the contents of which are incorporated herein by reference, discloses the use of 1,3,5,-substituted, 6,7-dihydro-1H-pyrazolo[4,3-d]pyrimidin-7-one compounds for treatment of diseases involving disorders of the dopamine D1 receptor intracellular pathway, but does not specifically disclose the use of such compounds in the treatment or prophylaxis of narcolepsy. PCT/US2006/022066, the contents of which are incorporated herein by reference, discloses PDE1 inhibitors which are 7,8-dihydro-[1H or 2H]-imidazo[1,2-a]pyrazolo[4,3-e]pyrimidin-4(5H)-ones or 7,8,9-trihydro-[1H or 2H]-pyrimido[1,2-a]pyrazolo[4,3-e]pyrimidin-4(5H)-ones, but does not specifically disclose their use for the treatment or prophylaxis of narcolepsy. WO 03/042216, U.S. Pat. No. 5,939,419, EP 0 538 332, U.S. Pat. No. 5,393,755, U.S. Pat. No. 6,969,719 B2, Xia et al., *J. Med. Chem.* (1997), 40, 4372-4377 and Ahn et al., *J. Med. Chem.* (1997), 40, 2196-2210, the contents of all of which are incorporated herein by reference, disclose PDE1 cGMP phosphodiesterase inhibitors which are substituted pyrazolo[3,4-d]pyrimidine, pyrimido[2,1-b]purin-4-one and imidazo[2,1-b]purin-4-one analogues useful for the treatment of hypertensive, cardiovascular, sexual dysfunction and other cGMP-PDEV related disorders, but do not specifically disclose their use for the treatment or prophylaxis of narcolepsy.

SUMMARY OF THE INVENTION

The invention provides a new method of treatment or prophylaxis for narcolepsy comprising administering an effective amount of a phosphodiesterase-1 (PDE1) inhibitor to a patient in need thereof. PDE1 inhibitors include, for example, 7,8-dihydro-[1H or 2H]-imidazo[1,2-a]pyrazolo[4,3-e]pyrimidin-4(5H)-ones or 7,8,9-trihydro-[1H or 2H]-pyrimido[1,2-a]pyrazolo[4,3-e]pyrimidin-4(5H)-ones, substituted at the 1 or 2 position with $C_{2-9}$ alkyl or $C_{3-9}$ cycloalkyl, or optionally substituted heteroarylalkyl or substituted arylalkyl, in free, salt or prodrug form (hereinafter a PDE 1 Inhibitor, e.g., as described below) or a 1,3,5-substituted 6,7-dihydro-1H-pyrazolo[4,3-d]pyrimidin-7-one, in free, salt or prodrug form (also included in PDE 1 Inhibitors, e.g., as described below), to a patient in need thereof.

PDE1 inhibitors also include, for example, substituted imidazo[2,1-b]purin-4-one, e.g., (6aR,9aS)-2-(biphenyl-4-ylmethyl)-5,6a,7,8,9,9a-hexahydro-5-methyl-3(phenylmethyl)-cyclopent-[4,5]imidazo-[2,1-b]purin-4(3H)-one, (6aR,9aS)-5,6a,7,8,9,9a-hexahydro-5-methyl-2,3-bis(phenylmethyl)cyclopent-[4,5]imidazo-[2,1-b]purin-4(3H)-one, 5'-methyl-2',3'-bis(phenylmethyl)spiro[cyclopentane-1,7'(8'H)-[3H]imidazo[2,1-b]purin]-4'(5'H)-one, or 5'-methyl-2'-(biphenylylmethyl)-3'-(phenylmethyl)spiro[cyclopentane-1,7'(8'H)-[3H]imidazo[2,1-b]purin]-4'(5'H)-one as described in Ahn et al., *J. Med. Chem.* (1997), 40, 2196-2210 (hereinafter a PDE 1 Inhibitor, e.g., as described below). These compounds are found to selectively inhibit phosphodiesterase 1 (PDE1) activity, especially PDE1B activity, and to be useful in the treatment and prophylaxis of narcolepsy. These compounds are found to selectively inhibit phosphodiesterase 1 (PDE1) activity, especially PDE1B activity, and to be useful in the treatment and prophylaxis of narcolepsy.

DETAILED DESCRIPTION OF THE INVENTION

Compounds for Use in the Methods of the Invention

Preferably, the PDE 1 Inhibitors for use in the methods of treatment described herein are a 7,8-dihydro-[1H or 2H]-imidazo[1,2-a]pyrazolo[4,3-e]pyrimidin-4(5H)-ones or 7,8,9-trihydro-[1H or 2H]-pyrimido[1,2-a]pyrazolo[4,3-e]pyrimidin-4(5H)-ones, of formula I

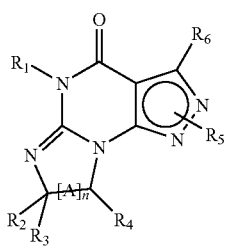

Formula I wherein
(i) $R_1$ is H or $C_{1-4}$ alkyl (e.g., methyl);
(ii) $R_4$ is H or $C_{1-4}$ alkyl and $R_2$ and $R_3$ are, independently, H or $C_{1-4}$ alkyl (e.g., $R_2$ and $R_3$ are both methyl, or $R_2$ is H and $R_3$ is isopropyl), aryl, heteroaryl, (optionally hetero)arylalkoxy, or (optionally hetero)arylalkyl;
or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(iii) $R_5$ is a substituted heteroarylalkyl, e.g., substituted with haloalkyl
or
$R_5$ is attached to one of the nitrogen atoms on the pyrazolo portion of Formula I and is a moiety of Formula Q

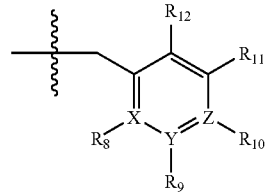

Formula Q wherein X, Y and Z are, independently, N or C, and $R_8$, $R_9$, $R_{11}$ and $R_{12}$ are independently H or halogen (e.g., Cl or F), and $R_{10}$ is halogen, alkyl, cycloalkyl, haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, $R_8$, $R_9$, or $R_{10}$, respectively, is not present; and
(iv) $R_6$ is H, alkyl, aryl, heteroaryl, arylalkyl (e.g., benzyl), arylamino (e.g., phenylamino), heteroarylamino, N,N-dialkylamino, N,N-diarylamino, or N-aryl-N-(arylalkyl)amino (e.g., N-phenyl-N-(1,1'-biphen-4-ylmethyl)amino); and
(v) n=0 or 1;
(vi) when n=1, A is —$C(R_{13}R_{14})$—
wherein $R_{13}$ and $R_{14}$, are, independently, H or $C_{1-4}$ alkyl, aryl, heteroaryl, (optionally hetero)arylalkoxy or (optionally hetero)arylalkyl;
in free, salt or prodrug form, including its enantiomers, diasterisomers and racemates.

The invention further provides the use of PDE 1 Inhibitors of Formula I as follows:
1.1 Formula I wherein $R_1$ is methyl and n=0;
1.2 Formula I or 1.1 wherein $R_4$ is H or $C_{1-4}$ alkyl and at least one of $R_2$ and $R_3$ is lower alkyl, such that when the carbon carrying $R_3$ is chiral, it has the R configuration, e.g., wherein both $R_2$ and $R_3$ are methyl, or wherein one is hydrogen and the other isopropyl;
1.3 Formula I or 1.1 wherein $R_4$ is H and at least one of $R_2$ and $R_3$ is arylalkoxy;
1.4 Formula I wherein $R_1$ is methyl, $R_2$, $R_3$, and $R_4$ are H, n=1, and $R_{13}$ and $R_{14}$ are, independently, H or $C_{1-4}$ alkyl (e.g., methyl or isopropyl);
1.5 Formula I or 1.1 wherein $R_2$ is H and $R_3$ and $R_4$ together form a tri- or tetramethylene bridge, having the cis configuration, preferably wherein the carbons carrying $R_3$ and $R_4$ have the R and S configurations respectively;

1.6 Formula I, 1.1 or 1.5 wherein $R_5$ is a substituted heteroarylmethyl, e.g., para-substituted with haloalkyl;

1.7 Formula I, 1.1, 1.2, 1.3, 1.4 or 1.5 wherein $R_5$ is a moiety of Formula Q wherein $R_8$, $R_9$, $R_{11}$, and $R_{12}$ are H and $R_{10}$ is phenyl;

1.8 Formula I, 1.1, 1.2, 1.3, 1.4 or 1.5 wherein $R_5$ is a moiety of Formula Q wherein $R_8$, $R_9$, $R_{11}$, and $R_{12}$ are H and $R_{10}$ is pyridyl or thiadiazolyl;

1.9 Formula I, 1.1, 1.2, 1.3, 1.4 or 1.5 wherein $R_5$ is a moiety of Formula Q wherein $R_8$, $R_9$, $R_{11}$, and $R_{12}$ are, independently, H or halogen, and $R_{10}$ is haloalkyl;

1.10 Formula I, 1.1, 1.2, 1.3, 1.4 or 1.5 wherein $R_5$ is a moiety of Formula Q wherein $R_8$, $R_9$, $R_{11}$, and $R_{12}$ are, independently, H, and $R_{10}$ is alkyl sulfonyl;

1.11 any of the preceding formulae wherein $R_5$ is attached to the 2-position nitrogen on the pyrazolo ring;

1.12 any of the preceding formulae wherein $R_6$ is benzyl;

1.13 any of the preceding formulae wherein $R_6$ is phenylamino or phenylalkylamino (e.g., benzylamino);

1.14 any of the preceding formulae wherein $R_6$ is phenylamino;

1.15 any of the preceding formulae wherein X, Y, and Z are all C, 1.16 any of the preceding formulae wherein X, Y, and Z are all C and $R_{10}$ is phenyl or 2-pyridyl; and/or 1.17 any of the preceding formulae wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 1;

in free or salt form.

For example, the PDE 1 Inhibitors include 7,8-dihydro-[1H or 2H]-imidazo[1,2-a]pyrazolo[4,3-e]pyrimidin-4(5H)-ones of Formula Ia

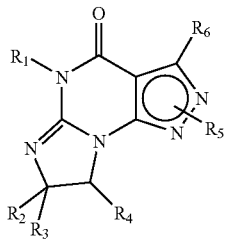

Formula Ia wherein
(i) $R_1$ is H or $C_{1-4}$ alkyl [e.g., methyl];
(ii) $R_4$ is H and $R_2$ and $R_3$ are, independently, H or $C_{1-4}$ alkyl [e.g., $R_2$ and $R_3$ are both methyl, or $R_2$ is H and $R_3$ is isopropyl], aryl, or arylalkyl;
or $R_2$ is H and $R_3$ and $R_4$ together form a di-, tri- or tetramethylene bridge [pref. wherein the $R_3$ and $R_4$ have the cis configuration, e.g., where the carbons carrying $R_3$ and $R_4$ have the R and S configurations respectively];
(iii) $R_5$ is attached to one of the nitrogen atoms on the pyrazolo portion of formula Ia and is a substituted benzyl of formula Qa

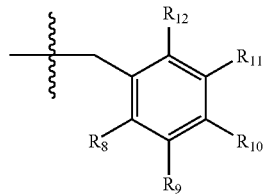

Formula Qa wherein $R_8$, $R_9$, $R_{11}$ and $R_{12}$ are independently H or halogen (e.g., Cl or F); and $R_{10}$ is halogen, alkyl, cycloalkyl, haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), arylcarbonyl (e.g., benzoyl), alkyl sulfonyl or heteroarylcarbonyl; and (iv) $R_6$ is H, alkyl, aryl, heteroaryl, arylalkyl [e.g., benzyl], arylamino [e.g., phenylamino], heteroarylamino, arylalkylamino, N,N-dialkylamino, N,N-diarylamino, or N-aryl-N-(arylalkyl)amino [e.g. N-phenyl-N-(1,1'-biphen-4-ylmethyl)amino];

in free, salt or prodrug form.

The invention further provides the use of PDE 1 Inhibitors of Formula Ia as follows:

2.1: Formula Ia wherein $R_1$ is methyl;

2.2: Formula Ia or 2.1 wherein $R_4$ is H and at least one of $R_2$ and $R_3$ is lower alkyl, such that when the carbon carrying $R_3$ is chiral, it has the R configuration, e.g., wherein both $R_2$ and $R_3$ are methyl, or wherein one is hydrogen and the other isopropyl;

2.3: Formula Ia or 2.1 wherein $R_2$ is H and $R_3$ and $R_4$ together form a tri- or tetramethylene bridge, having the cis configuration, preferably wherein the carbons carrying $R_3$ and $R_4$ have the R and S configurations respectively;

2.4: Formula Ia, 2.1, 2.2 or 2.3 wherein $R_5$ is a moiety of formula Qa wherein $R_8$, $R_9$, $R_{11}$, and $R_{12}$ are H and $R_{10}$ is phenyl;

2.5: Formula Ia, 2.1, 2.2, or 2.3 wherein $R_5$ is a moiety of formula Qa wherein $R_8$, $R_9$, $R_{11}$, and $R_{12}$ are H and $R_{10}$ is pyridyl or thiadiazolyl;

2.6: Formula Ia, 2.1, 2.2, 2.3, 2.4, or 2.5 wherein $R_5$ is attached to the 2-position nitrogen on the pyrazolo ring;

2.7: Formula Ia, 2.1, 2.2, 2.3, 2.4, 2.5 or 2.6 wherein $R_6$ is benzyl;

2.8: Formula Ia, 2.1, 2.2, 2.3, 2.4, 2.5 or 2.6 wherein $R_6$ is phenylamino or phenylalkylamino (e.g., benzylamino); and/or 2.9: Formula Ia, 2.1, 2.2, 2.3, 2.4, 2.5, 2.6, 2.7, or 2.8 wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 1;

in free or salt form.

In an another embodiment, the PDE 1 Inhibitors are compounds of Formula I wherein
(i) $R_1$ is methyl;
(ii) $R_2$, $R_3$ and $R_4$ are H;
(iii) n=1 and $R_a$ and $R_b$ are, independently, H or methyl;
(iv) $R_5$ is a moiety of Formula Q wherein $R_8$, $R_9$, $R_{11}$ and $R_{12}$ are H and $R_{10}$ is phenyl, pyridyl (for example pyrid-2-yl), or thiadiazolyl (e.g., 1,2,3-thiadiazol-4-yl);
(v) $R_6$ is benzyl, phenylamino or benzylamino;
in free or salt form.

In another embodiment, the PDE 1 Inhibitors are compounds of Formula I wherein
(i) $R_1$ is methyl;
(ii) n=0;
(iii) $R_2$ is H and $R_3$ and $R_4$ together form a tri- or tetramethylene bridge [pref. with the carbons carrying $R_3$ and $R_4$ having the R and S configuration respectively]; or at least one of $R_2$ and $R_3$ is methyl, isopropyl or arylalkoxy and $R_4$ is H; or $R_2$ and $R_3$ are H and $R_4$ is a $C_{1-4}$ alkyl;
(iv) $R_5$ is a substituted heteroarylmethyl, e.g., para-substituted with haloalkyl; or
$R_5$ is a moiety of Formula Q wherein $R_8$, $R_9$, $R_{11}$ and $R_{12}$ are H or halogen and $R_{10}$ is haloalkyl, phenyl, pyridyl (for example pyrid-2-yl), or thiadiazolyl (e.g., 1,2,3-thiadiazol-4-yl); and
(v) $R_6$ is benzyl, phenylamino or benzylamino;
in free or salt form.

In another embodiment, the PDE 1 Inhibitors are compounds of Formula Ia wherein
(i) $R_1$ is methyl;
(ii) $R_2$ is H and $R_3$ and $R_4$ together form a tri- or tetramethylene bridge [pref. with the carbons carrying $R_3$ and $R_4$ having the R and S configuration respectively]; or $R_2$ and $R_3$ are each methyl and $R_4$ is H; or $R_2$ and $R_4$ are H and $R_3$ is isopropyl [pref. the carbon carrying $R_3$ having the R configuration];
(iii) $R_5$ is a moiety of Formula Qa wherein $R_8$, $R_9$, $R_{11}$, and $R_{12}$ are H and $R_{10}$ is haloalkyl, phenyl, pyridyl (for example pyrid-2-yl), or thiadiazolyl (e.g., 1,2,3-thiadiazol-4-yl); and
(iv) $R_6$ is benzyl, phenylamino or benzylamino;
in free or salt form.

In another embodiment, the PDE 1 Inhibitors are compounds of Formula Ia selected from the following:

Compound 1

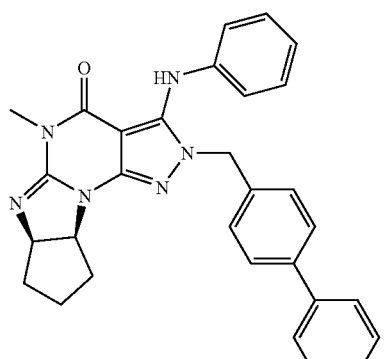

Compound 2

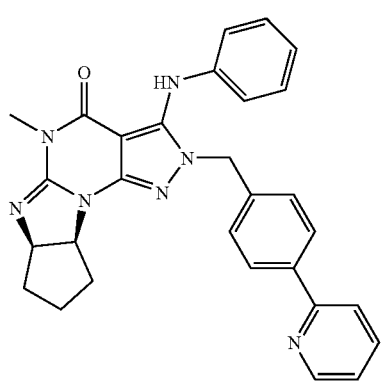

For example, PDE 1 Inhibitors include compounds according to Formulae II, III and IV.

Formula II

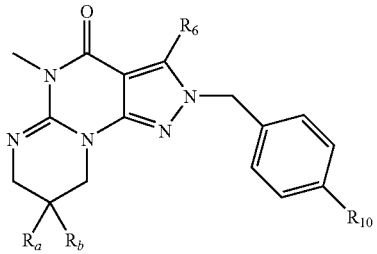

wherein
$R_a$ and $R_b$ are, independently, H or $C_{1-4}$ alkyl;
$R_6$ is phenylamino or benzylamino;
$R_{10}$ is phenyl, pyridyl (for example pyrid-2-yl), or thiadiazolyl (e.g., 1,2,3-thiadiazol-4-yl);
in free or salt form.

Formula III

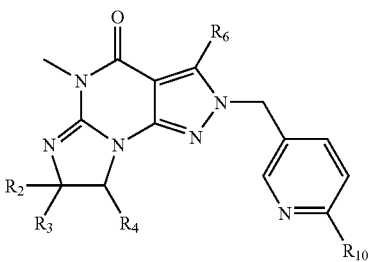

wherein
$R_2$ is H and $R_3$ and $R_4$ together form a tri- or tetra-methylene bridge [pref. with the carbons carrying $R_3$ and $R_4$ having the R and S configuration respectively]; or at least one of $R_2$ and $R_3$ is methyl, isopropyl or arylalkoxy and $R_4$ is H; or $R_2$ and $R_3$ are H and $R_4$ is a $C_{1-4}$ alkyl;
$R_6$ is phenylamino or benzylamino;
$R_{10}$ is haloalkyl, phenyl, pyridyl (for example pyrid-2-yl), or thiadiazolyl (e.g., 1,2,3-thiadiazol-4-yl);
in free or salt form.

Formula IV

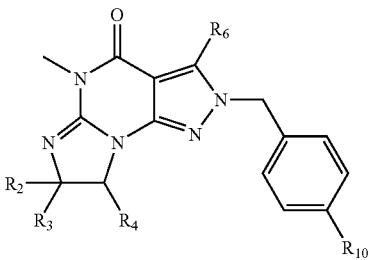

wherein
$R_2$ is H and $R_3$ and $R_4$ together form a tri- or tetra-methylene bridge [pref. with the carbons carrying $R_3$ and $R_4$ having the R and S configuration respectively]; or at least one of $R_2$ and $R_3$ is methyl, isopropyl or arylalkoxy and $R_4$ is H; or $R_2$ and $R_3$ are H and $R_4$ is a $C_{1-4}$ alkyl;
$R_6$ is phenylamino or benzylamino;
$R_{10}$ is phenyl, pyridyl (for example pyrid-2-yl), or thiadiazolyl (e.g., 1,2,3-thiadiazol-4-yl);
in free or salt form.

PDE 1 Inhibitors used in the method disclosed herein also include compounds according to Formula V:

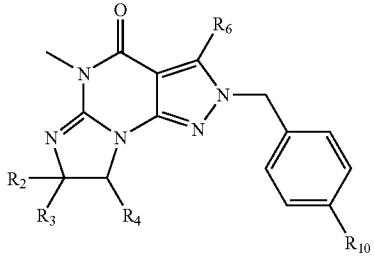

Formula V wherein
$R_2$ is H and $R_3$ and $R_4$ together form a tri- or tetra-methylene bridge [pref. with the carbons carrying $R_3$ and $R_4$ having the R and S configuration respectively]; or
$R_2$ and $R_3$ are each methyl and $R_4$ is H; or $R_2$ and $R_4$ are H and $R_3$ is isopropyl [pref. the carbon carrying $R_3$ having the R configuration];
$R_6$ is phenylamino or benzylamino;
$R_{10}$ is phenyl, pyridyl, or thiadiazolyl;
in free or salt form.

In a preferred embodiment, the PDE 1 Inhibitors for use in the methods of treatment described herein are a 1,3,5-substituted 6,7-dihydro-1H-pyrazolo[4,3-d]pyrimidin-7-one, of formula VI

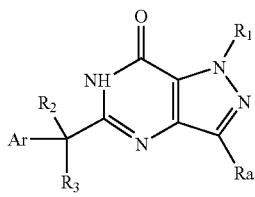

Formula VI wherein
$R_a$ is methyl or $C_2$-$C_6$ alkyl;
$R_1$ is H or $C_1$-$C_4$ alkyl;
each of $R_2$ and $R_3$ is independently selected from H and $C_1$-$C_4$ alkyl, or $R_2$ is H or $C_1$-$C_4$ alkyl and $R_3$ is OH, $C_2$-$C_4$ alkanoyloxy or fluoro, or $R_2$ and $R_3$ when taken together represent $C_2$-$C_6$ alkylene, or $R_2$ and $R_3$ when taken together with the carbon atom to which they are attached represent a carbonyl group;
Ar is either (a)

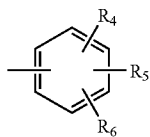

wherein
each of $R_4$, $R_5$ and $R_6$ is independently selected from
  H
  $C_1$-$C_4$ alkyl,
  $C_1$-$C_4$ alkoxy,
  $C_1$-$C_4$ alkoxy-Z—,
  halo,
  halo($C_1$-$C_4$)alkyl,
  phenoxy, optionally substituted by up to three substitutents each of which substitutent is independently selected from halo, $C_{1-4}$ alkyl, and $C_1$-$C_4$ alkoxy,
  nitro,
  hydroxy,
  hydroxy-Z—,
  $C_2$-$C_4$ alkanoyl,
  amino,
  amino-Z—,
  ($C_1$-$C_4$ alkyl)NH,
  ($C_1$-$C_4$ alkyl)$_2$N—,
  ($C_1$-$C_4$ alkyl)NH—Z—,
  ($C_1$-$C_4$ alkyl)$_2$N—Z—,
  —COOH,
  —Z—COOH,
  —COO($C_1$-$C_4$ alkyl),
  —Z—COO($C_1$-$C_4$ alkyl)
  $C_1$-$C_4$ alkanesulphonamido,
  $C_1$-$C_4$ alkanesulphonamido-Z—,
  halo($C_1$-$C_4$)alkanesulphonamido,
  halo($C_1$-$C_4$)alkanesulphonamido-Z—,
  $C_1$-$C_4$ alkanamido,
  $C_1$-$C_4$ alkanamido-Z—,
  HOOC—Z—NH—,
  HOOC—Z—NH—Z—,
  ($C_1$-$C_4$ alkyl)OOC—Z—NH—,
  ($C_1$-$C_4$ alkyl)OOC—Z—NH—Z—,
  $C_1$-$C_4$ alkyl-NH—SO$_2$—NH—,
  $C_1$-$C_4$ alkyl-NH—SO$_2$—NH—Z—,
  ($C_1$-$C_4$ alkyl)$_2$-N—SO$_2$—NH—,
  ($C_1$-$C_4$ alkyl)$_2$-N—SO$_2$—NH—Z—,
  $C_1$-$C_4$ alkoxy CH=CH—Z—CONH—,
  $C_1$-$C_4$ alkoxy CH=CHCONH
  $C_1$-$C_4$ alkyl-SO$_2$—N($C_1$-$C_4$ alkyl)-,
  $C_1$-$C_4$ alkyl-SO$_2$—N($C_1$-$C_4$ alkyl)-Z—,
  ($C_1$-$C_4$ alkyl)NH—Z—SO$_2$—NH—,
  ($C_1$-$C_4$ alkyl)$_2$N—Z—SO$_2$—NH—,
  ($C_1$-$C_4$ alkyl)NH—Z—SO$_2$—NH—Z—,
  ($C_1$-$C_4$ alkyl)$_2$N—Z—SO$_2$—NH—Z—,
  benzenesulphonamido, optionally ring substituted by up to three substitutents each of which is independently selected from halo, $C_{1-4}$ alkyl, and $C_1$-$C_4$ alkoxy,
  $C_1$-$C_4$ alkanoyl-N($C_1$-$C_4$ alkyl)-,
  $C_1$-$C_4$ alkanoyl-N($C_1$-$C_4$ alkyl)-Z—,
  $C_1$-$C_4$ alkoxycarbonyl-CH(CH$_2$OH)NHSO$_2$—,
  —SO$_3$H,
  —SO$_2$NH$_2$,
  H$_2$NOC—CH(CH$_2$OH)—NHSO$_2$—,
  HOOC—Z—O—, and
  ($C_1$-$C_4$ alkyl)OOC—Z—O—,
or optionally one of $R_4$, $R_5$ and $R_6$ is a G-Het group and wherein the others of $R_4$, $R_5$ and $R_6$ are independently selected from the $R_4$, $R_5$ and $R_6$ substitutents listed above;
Z is $C_1$-$C_4$ alkylene,
G is a direct link, Z, O, —SO$_2$NH—, SO$_2$, or —Z—N($C_1$-$C_4$ alkyl)SO$_2$—,
Het is a 5- or 6-membered heterocyclic group containing 1, 2, 3 or 4 nitrogen heteroatoms; or 1 or 2 nitrogen heteroatoms and 1 sulphur heteroatom or 1 oxygen heteroatom; or the heterocyclic group is furanyl or thiophenyl; wherein the Het group is saturated or partially or fully unsaturated and optionally substituted by up to 3 substitutents, wherein each substituent is independently selected from $C_1$-$C_4$ alkyl, oxo, hydroxy, halo, and halo ($C_1$-$C_4$) alkyl;
or (b) any one of the following bicyclic groups:
 benzodioxolanyl,
 benzodioxanyl,
 benzimidazolyl,
 quinolinyl,
 indolyl,
 quinazolinyl,
 isoquinolinyl,
 benzotriazolyl,
 benzofuranyl,
 benzothiophenyl,
 quinoxalinyl, or
 phthalazinyl,
wherein said bicyclic Ar groups are linked to the neighbouring —C($R_2R_3$)— group via the benzo ring portion, and wherein the heterocyclic portion of said bicyclic Ar group is optionally partially or fully saturated, said group being optionally substituted by one or more of $C_1$-$C_4$ alkyl, halo, hydroxy, oxo, amino, and $C_1$-$C_4$ alkoxy;
or a pharmaceutically acceptable salt of the compound, or a pharmaceutically acceptable solvate of the compound or the salt.

For example, PDE 1 Inhibitors for use in the present invention include 1,3,5,-substituted, 6,7-dihydro-1H-pyrazolo[4,3-d]pyrimidin-7-one, in free or pharmaceutically acceptable salt form, particularly compounds of Formula VI or the following formulae:
 3.2 Of Formula VI wherein $R_a$ is a $C_{2-5}$ alkyl group;
 3.3 Of Formula VI wherein $R_a$ is a $C_{2-4}$ alkyl group;
 3.4 Of Formula VI wherein $R_a$ is a $C_3$ alkyl group;
 3.5 Of Formula VI wherein $R_a$ is methyl;
 3.6 Of Formula VI, 3.2, 3.3, 3.4 or 3.5 wherein $R_1$ is a $C_{1-6}$ alkyl group;
 3.7 Of any of the preceding formulae wherein $R_1$ is a $C_{1-3}$ alkyl group;
 3.8 Of any of the preceding formulae wherein $R_1$ is a methyl group;
 3.9 Of any of the preceding formulae wherein $R_2$ is H,
 3.10 Of any of the preceding formulae wherein $R_3$ is H,
 3.11 Of any of the preceding formulae wherein $R_4$, $R_5$ and $R_6$ are independently selected from H, ($C_{1-4}$ alkyl)$_2$N—, $C_{1-4}$ alkanesulphonamido and benzenesulphonamido;
 3.12 Of any of the preceding formulae wherein $R_4$, $R_5$ and $R_6$ are independently selected from H, diethylamino, methanesulphonamido and benzenesulphonamido;
 3.13 Of any of the preceding formulae wherein Ar is 4-diethylaminophenyl;
 3.14 Of any of the preceding formulae wherein Ar is 2-methanesulphonamidophenyl;
 3.15 Of any of the preceding formulae wherein Ar is 4-benzenesulphonamidophenyl;
 3.16 Of any of the preceding formulae wherein one of $R_4$, $R_5$ and $R_6$ is ($C_{1-4}$ alkyl)$_2$N— and wherein the other two of $R_4$, $R_5$ and $R_6$ are H.
 3.17 Of any of the preceding formulae wherein one of $R_4$, $R_5$ and $R_6$ is diethylamino and wherein the other two of $R_4$, $R_5$ and $R_6$ are H.
 3.18 Of any of the preceding formulae wherein $R_a$ is methyl;
 3.19 Of any of the preceding formulae wherein $R_a$ is $C_2$-$C_6$ alkyl;
 3.20 Of any of the preceding formulae wherein the compound is selected from the following:

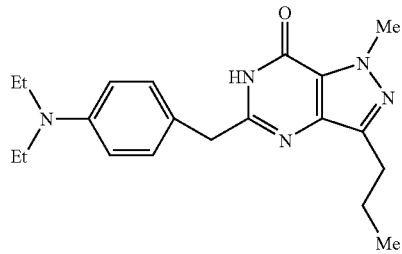

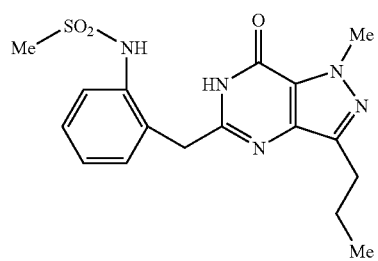

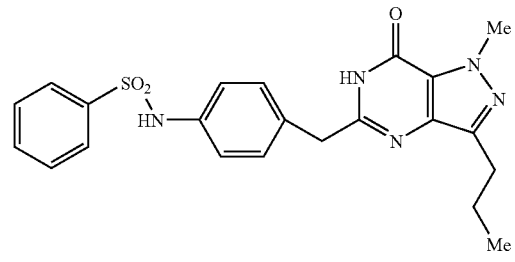

3.21 Of any of the preceding formulae wherein the compound is

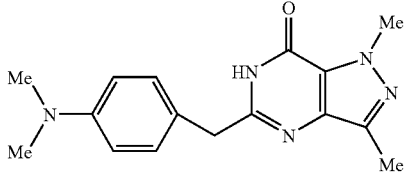 [SMILES: Cc1nn(C)c2c(=O)[nH]c(Cc3ccc(N(C)C)cc3)nc12]

in free or salt form;
 3.22 A compound which is a 1,3,5,-substituted, 6,7-dihydro-1H-pyrazolo[4,3-d]pyrimidin-7-one, in free or pharmaceutically acceptable salt form, e.g. a compound of Formula VI or according to any of formulae 3.2-3.21, wherein the compound inhibits phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 1 below.

In another embodiment, the PDE 1 Inhibitors for use in the methods of treatment described herein are substituted (imidazo, pryimido or diazepino)[2,1-b]purin-4-ones of Formula VIIa or VIIb:

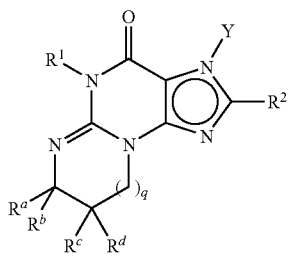

Formula VIIa

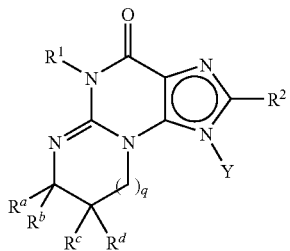

Formula VIIb in free, salt or prodrug form, including its enantiomers, diasterisomers and racemates, wherein:

i) q=0, 1 or 2;
ii) $R^1$, $R^a$, $R^b$, $R^c$ and $R^d$ are each independently H, alkyl, aryl, heteroaryl, cycloalkyl or heterocycloalkyl groups,
wherein each alkyl group of $R^1$, $R^a$, $R^b$, $R^c$ and $R^d$ is independently unsubstituted or substituted with 1 to 5 independently selected $R^3$ moieties which can be the same or different, each $R^3$ moiety being independently selected from the group consisting of hydroxy, alkoxy, cycloalkoxy, aryloxy, alkylthio, arylthio, aryl, haloaryl, heteroaryl, cycloalkyl, heterocycloalkyl, amino, alkylamino, dialkylamino, cycloalkylamino and heterocycloalkylamino groups;
wherein each of the aryl, heteroaryl, cycloalkyl and heterocycloalkyl groups of $R^1$, $R^a$, $R^b$, $R^c$ and $R^d$ is independently unsubstituted or substituted with 1 to 5 independently selected $R^4$ moieties which can be the same or different, each $R^4$ moiety being independently selected from the group consisting of: halo, optionally substituted aryl (e.g., phenyl, chlorophenyl, methoxyphenyl), heteroaryl (e.g., pyridyl, pyrrolyl), nitro, cyano, haloalkyl, haloalkoxy, alkyl, alkoxy, cycloalkyl, heterocycloalkyl (e.g., pyrrolidinyl, morpholin-4-yl, pyrrol-1-yl), cycloalkylalkyl, amino, alkylamino, dialkylamino, —OCF₃, acyloxy, —OR⁸, —C(O)R⁹, —C(O)OR⁸, —NR¹⁰C(O)R⁹, —NR¹⁰C(O)OR⁸, —NR¹⁰S(O)₂R⁹, —S(O)₀₋₂R⁹ groups, carbonyl when two hydrogens attached to the same carbon atom of the cycloalkyl or heterocycloalkyl group of R' are substituted, and =CR⁸R⁹ when two hydrogens attached to the same carbon atom of the cycloalkyl or heterocycloalkyl groups of $R^1$ are substituted,
wherein each of the aryl, heteroaryl, cycloalkyl and heterocycloalkyl groups of the $R^3$ and $R^4$ moieties above is independently unsubstituted or substituted with 1 to 5 independently selected $R^{12}$ moieties which can be the same or different, each $R^{12}$ moiety being independently selected from the group consisting of: halo, phenyl, nitro, cyano, haloalkyl, haloalkoxy, alkyl, cycloalkyl, cycloalkylalkyl, amino, alkylamino, —OCF₃, acyloxy, —OR⁸, —C(O)R⁹, —C(O)OR⁸, —NR¹⁰C(O)R⁹, —NR¹⁰C(O)OR⁸, —NR¹⁰S(O)₂R⁹, —S(O)₀₋₂R⁹ groups, carbonyl when two hydrogens attached to the same carbon atom of the cycloalkyl or heterocycloalkyl group of $R^3$ or $R^4$ are substituted, and =CR⁸R⁹ when two hydrogens attached to the same carbon atom of the cycloalkyl or heterocycloalkyl group of $R^3$ or $R^4$ are substituted; or iii) $R^a$ and $R^b$, together with the carbon to which they are both attached, form a 4- to 7-membered cycloalkyl or heterocycloalkyl ring, and $R^c$ and $R^d$ are each independently H or an alkyl group; or iv) $R^a$ and $R^c$, together with the respective carbons to which they are attached, form a 4- to 7-membered cycloalkyl or heterocycloalkyl ring, and $R^b$ and $R^d$ are each independently H or an alkyl group, preferably $R^a$ and $R^c$ together have the cis configuration, e.g., where the carbons carrying $R^a$ and $R^c$ have the R and S configurations, respectively;

v) $R^2$ is H, halo, alkyl, haloalkyl, alkoxy, alkylthio, amino, aminosulfonyl, monoalkylamino, dialkylamino, hydroxyalkylamino, aminoalkylamino, carboxy, alkoxycarbonyl, aminocarbonyl or alkylaminocarbonyl group,
wherein each alkyl group of $R^2$ is independently unsubstituted or substituted with 1 to 5 independently selected $R^{13}$ moieties which can be the same or different, each $R^{13}$ moiety being independently selected from the group consisting of halo, hydroxy, alkoxy, alkyl, aryl (e.g., phenyl, naphthyl) heteroaryl (e.g., 1H-imidazol-2-yl), cycloalkyl, heterocycloalkyl (e.g., pyrrolidin-1-yl), amino, monoalkylamino or dialkylamino group,
wherein each aryl group of $R^{13}$ is independently unsubstituted or substituted with 1 to 5 independently selected $R^4$ moieties which can be the same or different;

vi) Y is H or an alkyl group substituted with (i) an aryl, heteroaryl, cycloalkyl, hydroxy, alkoxy, amino, monoalkylamino or dialkylamino group, or (ii) an aryl group substituted with from one to three moieties each independently selected from the group consisting of: halo, alkyl, phenyl, hydroxy, alkoxy, phenoxy, amino, monoalkylamino and dialkylamino group;

vii) each $R^8$ is independently H, alkyl or aryl;
viii) each $R^9$ is independently H, alkyl, aryl or —NR¹⁰R¹¹;
ix) each $R^{10}$ is independently H, alkyl, aryl, heteroaryl, arylalkyl or heteroarylalkyl, wherein each alkyl, aryl, heteroaryl, arylalkyl or heteroarylalkyl of $R^{10}$ is unsubstituted or independently substituted with 1 to 5 $R^{14}$ moieties which can be the same or different, each $R^{14}$ moiety being independently selected from the group consisting of: halo, alkyl, aryl, cycloalkyl, —CF₃, —OCF₃, —CN, —OR⁸, —CH₂OR⁸, —C(O)OR⁸ and —C(O)NR⁸R⁸; and x) each $R^{11}$ is independently H, alkyl, aryl, heteroaryl, arylalkyl or heteroarylalkyl, wherein each alkyl, aryl, heteroaryl, arylalkyl or heteroarylalkyl of $R^{11}$ is unsubstituted or independently substituted with 1 to 5 $R^{14}$ moieties which can be the same or different.

The invention further provides the use of PDE 1 Inhibitors of Formula VIIa or VIIb, in free or salt form, as follows:

4.1: Formula VIIa or VIIb, wherein q=0, 1 or 2;
4.2: Formula VIIa or VIIb, wherein q=0;
4.3: Formula VIIa or VIIb or 4.1 or 4.2, wherein $R_1$ is alkyl;
4.4: Formula VIIa or VIIb or 4.1-4.3, wherein $R^1$ is methyl;
4.5: Formula VIIa or VIIb or 4.1-4.4, wherein $R^a$ and $R^c$, together with the respective carbons to which they are attached, form a 4- to 7-membered cycloalkyl or heterocycloalkyl ring, and $R^b$ and $R^d$ are each independently H or an alkyl group;

4.6: Formula VIIa or VIIb or 4.1-4.4, wherein $R^a$ and $R^c$, together with the respective carbons to which they are attached, form a 5-membered heterocycloalkyl ring, and $R^b$ and $R^d$ are each independently H, 4.7: Formula 4.6 wherein $R^a$ and $R^c$ together have a cis configuration;

4.8: Formula VIIa or VIIb or 4.1-4.4, wherein $R^a$ and $R^b$, together with the respective carbons to which they are attached, form a 5-membered heterocycloalkyl ring, and $R^c$ and $R^d$ are each independently H, 4.9: Formula VIIa or VIIb or 4.1-4.7, wherein $R^2$ is alkyl or haloalkyl;

4.10: Formula VIIa or VIIb or 4.1-4.7, wherein $R^2$ is biphenyl-4-ylmethyl;

4.11: Formula VIIa or VIIb or 4.1-4.7, wherein $R^2$ is benzyl;

4.12: Formula VIIa or VIIb or 4.1-4.7, wherein $R^2$ is cyclopentylmethyl;

4.13: Formula VIIa or VIIb or 4.1-4.7, wherein $R^2$ is cyclopropylmethyl; and/or 4.14: Formula VIIa or VIIb or 4.1-4.12, wherein Y is benzyl;

4.15: Of any of the preceding formulae wherein the compound is selected from the following:

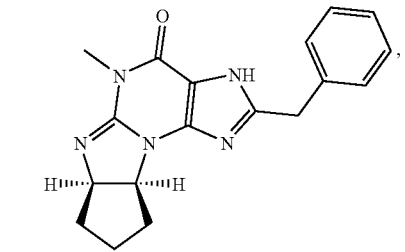

,

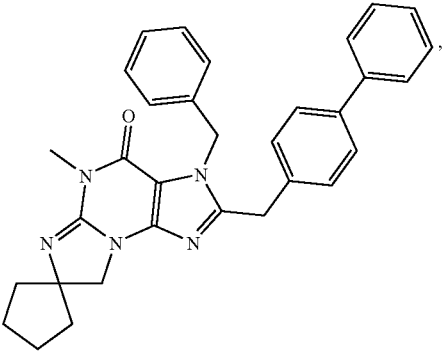

,

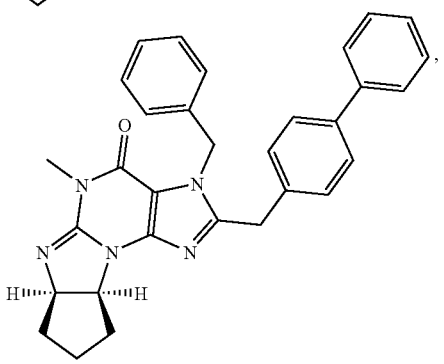

,

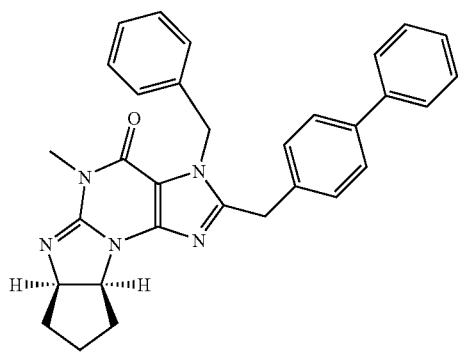 [SMILES: CN1C(=O)c2c(nc(Cc3ccc(-c4ccccc4)cc3)n2Cc2ccccc2)N2C1=N[C@@H]1CCC[C@@H]12]

, 4.16: Of any of the preceding formulae wherein the compound is

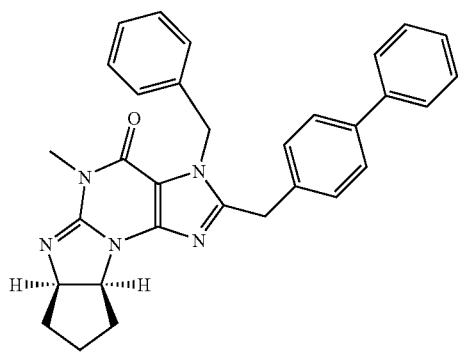 [SMILES: CN1C(=O)c2c(nc(Cc3ccc(-c4ccccc4)cc3)n2Cc2ccccc2)N2C1=N[C@@H]1CCC[C@@H]12]

in free or salt form;

4.17: A compound which is a substituted imidazo[2,1-b]purin-4-one, in free or pharmaceutically acceptable salt form, e.g. a compound of Formula VIIa or according to any of formulae 4.1-4.16, wherein the compound inhibits phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 1 below.

Preferably, compounds of Formula VIIa or VIIb are selected from a group consisting of (6aR,9aS)-5,6a,7,8,9,9a-hexahydro-5-methyl-2,3-bis(phenylmethyl)-cyclopent[4,5]imidazo[2,1-b]purin-4(3H)-one, (6aR,9aS)-2-(biphenyl-4-ylmethyl)-5,6a,7,8,9,9a-hexahydro-5-methyl-3-(phenylmethyl)cyclopent[4,5]imidazo[2,1-b]purin-4(3H)-one, 5'-methyl-2',3'-bis(phenylmethyl)spiro[cyclopentane-1,7'(8'H)-[3H]imidazo[2,1-b]purin]-4'(5'H)-one and 5'-methyl-2'-(biphenyl-4-ylmethyl)-3'-(phenylmethyl)spiro-

[cyclopentane-1,7'(8'H)-[3H]imidazo[2,1-b]purin]-4'(5'H)-one, in free or pharmaceutically acceptable salt form.

In an especially preferred embodiment, compound of Formula VIIa is (6aR,9aS)-2-(biphenyl-4-ylmethyl)-5,6a,7,8,9,9a-hexahydro-5-methyl-3-(phenylmethyl)cyclopent-[4,5]imidazo[2,1-b]purin-4(3H)-one, in free or salt form.

The numbering of substituted imidazo[2,1-b]purin-4-one of Formula VIIa or VIIb as described herein is shown below as an example, wherein q=0:

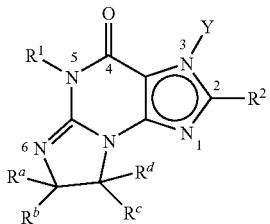
Formula VIIa wherein q=1:

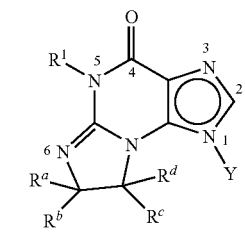
Formula VIIa

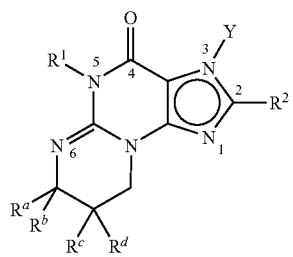
Formula VIIb

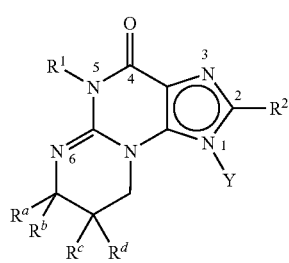
Formula VIIb

In another embodiment, the PDE 1 Inhibitors for use in the methods of treatment described herein are Compounds of Formula VIIIa or VIIIb:

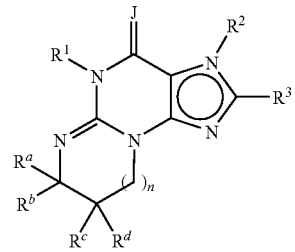
Formula VIIIa

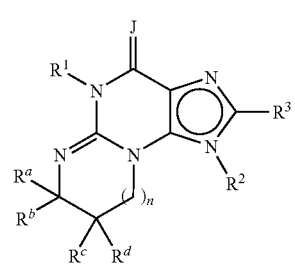
Formula VIIIb in free or salt form, wherein:
J is oxygen or sulfur,
$R^1$ is hydrogen, alkyl or alkyl substituted with aryl or hydroxy;
$R^2$ is hydrogen, aryl, heteroaryl, cycloalkyl, alkyl or alkyl substituted with aryl, heteroaryl, hydroxy, alkoxy, amino, monoalkyl amino or dialkylamino, or —$(CH_2)_m$TCOR$^{20}$ wherein m is an integer from 1 to 6, T is oxygen or —NH— and $R^{20}$ is hydrogen, aryl, heteroaryl, alkyl or alkyl substituted with aryl or heteroaryl;
$R^3$ is hydrogen, halo, trifluoromethyl, alkoxy, alkylthio, alkyl, cycloalkyl, aryl, aminosulfonyl, amino, monoalkylamino, dialkylamino, hydroxyalkylamino, aminoalkylamino, carboxy, alkoxycarbonyl or aminocarbonyl or alkyl substituted with aryl, hydroxy, alkoxy, amino, monoalkylamino or dialkylamino;
$R^a$, $R^b$, $R^c$ and $R^d$ independently represent hydrogen, alkyl, cycloalkyl or aryl; or ($R^a$ and $R^b$) or ($R^c$ and $R^d$) or ($R^b$ and $R^c$) can complete a saturated ring of 5- to 7-carbon atoms, or ($R^a$ and $R^b$) taken together and ($R^b$ and $R^c$) taken together, each complete a saturated ring of 5- to 7-carbon atoms, wherein each ring optionally can contain a sulfur or oxygen atom and whose carbon atoms may be optionally substituted with one or more or the following: alkenyl, alkynyl, hydroxy, carboxy, alkoxycarbonyl, alkyl or alkyl substituted with hydroxy, carboxy or alkoxycarbonyl; or such saturated ring can have two adjacent carbon atoms which are shared with an adjoining aryl ring; and
n is zero or one.

The invention further provides the use of PDE 1 Inhibitors of Formula VIIIa or VIIIb as follows:
 5.1: Formula VIIIa or VIIIb, wherein J=O
 5.2: Formula VIIIa or VIIIb or 5.1, wherein $R^1$ is alkyl.
 5.3: Formula VIIIa or VIIIb, 5.1 or 5.2, wherein $R^2$ is hydrogen, benzyl, 4-chlorobenzyl, cyclohexylmethyl or trimethylacetoxymethyl.
 5.4: Formula VIIIa or VIIIb, 5.1, 5.2 or 5.3, wherein $R^3$ is hydrogen, or alkyl such as methyl or ethyl.
 5.5: Formula VIIIa or VIIIb, 5.1, 5.2, 5.3 or 5.4, wherein n is zero; and
 5.6: Formula VIIIa or VIIIb, 5.1, 5.2, 5.3, 5.4 or 5.5, wherein $R^a$ and $R^b$ form a saturated 5 membered ring, or ($R^b$ and $R^c$) form a saturated 5, 6 or 7 membered ring, or ($R^a$ and $R^b$) and ($R^b$ and $R^c$) each complete a saturated ring and each ring contains 5 or 6 carbon atoms.

5.7 Formula VIIIa or VIIIb, in free or salt form, selected from the following:

cis-5,6a,7,8,9,9a-Hexahydro-5-methyl-3-(phenylmethyl)cyclopenta[4,5]imidazo-[2,1-b]purin-4-one;

7,8-Dihydro-5-methyl-3-(phenylmethyl)-3H-imidazo[2,1-b]purin-4(5H)-one;

cis-6a,7,8,9,10,10a-Hexahydro-5-methyl-3-(phenylmethyl)-3H-benzimidazo[2,1-b]purin-4(5H)-one;

5,7,8,9-Tetrahydro-5-methyl-3-(phenylmethyl)pyrimido[2,1-b]purin-4(3H)-one;

7,8-Dihydro-8-phenyl-5-methyl-3-(phenylmethyl)-3H-imidazo[2,1-b]purin-4(5H)-one;

5',7'-Dihydro-5'-methyl-3'-(phenylmethyl)spiro[cyclohexane-1,8'-(8H)imidazo-[2,1-b]purin]-4'(3'H)-one;

cis-5,6a,11,11a-Tetrahydro-5-methyl-3-(phenylmethyl)indeno[1',2':4,5]imidazo-[2,1-b]purin-4(3H)-one;

5',7'-Dihydro-2',5'dimethyl-3'-(phenylmethyl)spiro{cyclohexane-1,7'(8'H)-imidazo[2,1-b]purin}-4'-(3'H)-one;

7,8-Dihydro-2,5,7,7,8(R,S)-pentamethyl-3H-imidazo[2,1-b]purin-4(5H)-one;

cis-5,6a,7,11b-Tetrahydro-5-methyl-3-(phenylmethyl)indeno[2',1',4,5]imidazo[2,1-b]purin-4(3H)-one;

cis-5,6a,7,8,9,9a-Hexahydro-2,5-dimethyl-3-(phenylmethyl)cyclopent[4,5]-imidazo[2,1-b]purin-4-(3H)-one;

5'-Methyl-3'-(phenylmethyl)-spiro[cyclopentane-1,7'-(8'H)-(3'H)imidazo[2,1-b]purin]-4-(5'H)-one;

7,8-Dihydro-2,5,7,7-tetramethyl-3-(phenylmethyl)-3H-imidazo[2,1-b]purin-4(5'H)-one;

7,8-Dihydro-7(R)-phenyl-2,5-dimethyl-3-(phenylmethyl)-3H-imidazo[2,1-b]purin-4(5H)-one;

7,8-Dihydro-2,5-dimethyl-3,7(R)-bis(phenylmethyl)-3H-imidazo[2,1-b]purin-4(5H)-one;

(±)-7,8-Dihydro-2,5-dimethyl-7-ethyl-3-(phenylmethyl)-3H-imidazo[2,1-b]purin-4(5H)-one;

6a(S)-7,8,9,10,10a(R)-Hexhydro-2,5-dimethyl-3-(phenylmethyl)-3H-benzimidazo[2,1-b]purin-4(5H)-one;

6a(R)-7,8,9,10,10a(S)-hexahydro-2,5-dimethyl-3-(phenylmethyl)-3H-benzimidazo-[2,1-b]purin-4(5H)-one;

7,8-Dihydro-2,5-dimethyl-7(R)-isopropyl-3-(phenylmethyl)-3H-imidazo[2,1-b]purin-4(5H)-one;

7,8-Dihydro-2,5,7(R)-trimethyl-3-(phenylmethyl)-3H-imidazo[2,1-b]purin-4(5H)-one;

cis-7,7a,8,9,10,10a-Hexahydro-2,5-dimethyl-3-(phenylmethyl)-3H-cyclopenta-[5,6]pyrimido[2,1-b]purin-4(5H)-one;

7,8-Dihydro-2,5-dimethyl-7(S)-(1-methylpropyl)-3-(phenylmethyl)-3H-imidazo-[2,1-b]purin-4(5H)-one;

7,8-Dihydro-2,5-dimethyl-7(R)-(2-methylpropyl)-3-(phenylmethyl)-3H-imidazo-[2,1-b]purin-4(5H)-one;

7,8-Dihydro-2,5-dimethyl-7(R,S)-(methoxycarbonyl)-3-(phenylmethyl)-3H-imidazo[2,1-b]purin-4(5H)-one;

7,8-Dihydro-2,5-dimethyl-7(R,S)-(1-propyl)-3-(phenylmethyl)-3H-imidazo[2,1-b]purin-4(5H)-one;

7,8-Dihydro-2,5-dimethyl-7(S)-(1-methylethyl)-3-(phenylmethyl)-3H-imidazo[2,1-b]purin-4(5H)-one;

7,8-Dihydro-2,5,7,7,8(R,S)-pentamethyl-3H-imidazo[2,1-b]purin-4(5H)-one;

5,7,8,9-Tetrahydro-2,5,7,9(R,S)-pentamethyl-3-(phenylmethyl)-pyrimido[2,1-b]purin-4(3H)-one;

5,6a(R),7,8,9,9a(S)-Hexahydro-2,5-dimethyl-3-(phenylmethyl)cyclopent-[4,5]imidazo[2,1-b]purin-4(3H)-one;

5,6a(S),7,8,9,9a(R)-Hexahydro-2,5-dimethyl-3-(phenylmethyl)cyclopent-[4,5]imidazo[2,1-b]purin-4(3H)-one;

cis-6a,7,8,9,10,10a-Hexahydro-2,5-dimethyl-3-(phenylmethyl)-3H-benzimidazo[2,1-b]purin-4(5H)-one;

5',7'-Dihydro-2',5'-dimethyl-3'-(phenylmethyl)spiro[cyclohexane-1,8-(8H)-imidazo[2,1-b]purin]-4-(3'H)-one;

cis-5,6a,7,8,9,9a-Hexahydro-2,5-dimethyl-3-(phenylmethyl)cyclohept-[6,7]imidazo[2,1-b]purin-4(3H)-one;

cis-5,6a,7,8,9,9a-Hexahydro-5-methyl-2-ethyl-3-(phenylmethyl)cyclopent-[4,5]imidazo[2,1-b]purin-4(3H)-one;

cis-6a,7,8,9,10,10a-Hexahydro-5-methyl-2-ethyl-3-(phenylmethyl)-3H-benzimidazo[2,1-b]purin-4-(5H)-one;

cis-5,6a,7,8,9,9a-Hexahydro-5-methyl-2-ethyl-3-(phenylmethyl)cyclopent-[4,5]imidazo[2,1-b]purin-4(3H)-one;

cis-5,6a,7,8,9,9a-Hexahydro-5-methyl-2-phenyl-3-(phenylmethyl)cyclopent-[4,5]imidazo[2,1-b]purin-4(3H)-one;

cis-6a,7,8,9,10,10a-Hexahydro-5-methyl-2-phenyl-3-(phenylmethyl)-3H-benzimidazo[2,1-b]purin-4(5H)-one;

cis-5,6a,7,8,9,9a-Hexahydro-5-methylcyclopenta[4,5]imidazo[2,1-b]purin-4(3H)-one;

cis-5,6a,7,8,9,9a-Hexahydro-2,5-dimethylcyclopenta[4,5]imidazo[2,1-b]purin-4(3H)-one;

cis-5,6a(R), 7,8,9,9a(S)-Hexahydro-2,5-di-methylcyclopent[4,5]imidazo[2,1-b]purin-4(3H)-one;

2',5'-dimethyl-spiro{cyclopentane-1,7'-(8'H)-(3'H)-imidazo[2,1-b]purin}-4'(5'H)-one;

7,8-Dihydro-2,5-dimethyl-7(R)-(1-methylethyl)-3H-imidazo[2,1-b]purin-4(5H)-one;

7,8-Dihydro-2,5,7,7-tetramethyl-3H-imidazo[2,1-b]purin-4(5H)-one;

7,8-Dihydro-2,5-dimethyl-7(S)-(1-methylethyl)-3H-imidazo[2,1-b]purin-4(5H)-one;

6a(R),7,8,9,10,10a(S)-Hexahydro-2,5-dimethyl-3H-benzimidazo[2,1-b]purin-4(5H)-one;

5',7'-Dihydro-2',5'-dimethylspiro{cyclohexane-1,7-(8'H)-imidazo[2,1-b]purin}-4'(3'H)-one;

cis-5,6a,7,8,9,9a-Hexahydro-5-methyl-3-(phenylmethyl)cyclopenta[4,5]-imidazo[2,1-b]purin-4(3H)-thione;

5,6a(R),7,8,9,9a(S)-Hexahydro-2,5-dimethyl-3-(phenylmethyl)cyclopent-[4,5]imidazo[2,1-b]purin-4(3H)-thione;

cis-5,6a,7,8,9,9a-Hexahydro-5-methyl-3-(4-chlorophenylmethyl)cyclopenta[4,5]-imidazo[2,1-b]purin-4(3H)-one;

cis-5,6a,7,8,9,9a-Hexahydro-5-methyl-3-(cyclohexylmethyl)cyclopent[4,5]-imidazo[2,1-b]purin-4(3H)-one;

cis-5,6a,7,8,9,9a-Hexahydro-5-methyl-3-(2-naphthylmethyl)cyclopent[4,5]-imidazo[2,1-b]purin-4(3H)-one;

5,6a(R),7,8,9,9a(S)-Hexahydro-2,5-dimethyl-3-(4-bromophenylmethyl)-cyclopent[4,5]imidazo[2,1-b]purin-4(3H)-one;

5,6a(R)-7,8,9,9a(S)-Hexahydro-2,5-dimethyl-3-(4-methoxyphenylmethyl)-cyclopent[4,5]imidazo[2,1-b]purin-4(3H)-one;

cis-5,6a,7,8,9,9a-Hexahydro-2,3,5-trimethylcyclopent[4,5]imidazo[2,1-b]purin-4(3H)-one;

cis-5,6a,7,8,9,9a-Hexahydro-2-(hydroxymethyl)-5-methyl-3-(phenylmethyl)-cyclopent[4,5]imidazo[2,1-b]purin-4(3H)-one;

cis-5,6a,7,8,9,9a-Hexahydro-2-methylthio-5-methyl-3-(Phenylmethyl)cyclopent-[4,5]imidazo[2,1-b]purin-4(3H)-one;

cis-3,4,5,6a,7,8,9,9a-Octahydro-5-methyl-4-oxo-3-(phenylmethyl)cyclopent-[4,5]imidazo[2,1-b]purin-2-carboxylic acid;

cis-3,4,5,6a,7,8,9,9a-Octahydro-5-methyl-4-oxo-3-(phenylmethyl)cyclopent-[4,5]imidazo[2,1-b]purin-2-carboxylic acid, methyl ester;

cis-5,6a,7,8,9,9a-Hexahydro-2-bromo-5-methyl-3-(phenylmethyl)cyclopent[4,5]imidazo[2,1-b]purin-4(3H)one;

cis-5,6a,7,8,9,9a-Hexahydro-2-(methylaminosulfonyl)-5-methyl-3-(phenylmethyl)cyclopent[4,5]imidazo[2,1-b]purin-4(3H)one;
cis-1-Cyclopentyl-5,6a,7,8,9,9a-hexahydro-5-methylcyclopent[4,5]imidazo[2,1-b]purin-4-(1H)one;
cis-5,6a,7,8,9,9a-Hexahydro-3,5-bis-(phenylmethyl)cyclopent(4,5)imidazo[2,1-b]purin-4(3H)one;
cis-6a,7,8,9,10,10a-Hexahydro-3,5-bis-(phenylmethyl)-3H-benzimidazo[2,1-b]purin-4(5H)one;
cis-3-Cyclopentyl-5,6a,7,8,9,9a-hexahydro-5-methylcyclopent[4,5]imidazo[2,1-b]purin-4(3H)one;
5'-Methyl-3'-(phenylmethyl)spiro[cyclopentane-1,7-(8'H)-(3'H)imidazo[2,1-b]purin]-4-(5'H)one;
2',5'-Dimethyl-3'-(phenylmethyl)-spiro[cyclopentane-1,7-(8'H)-(3'H)imidazo[2,1-b]purin]-4-(5'H)one;
cis-5,6a,(R)7,8,9,9a(S)-Hexahydro-5-methyl-3-(phenylmethyl)cyclopent[4,5]-imidazo[2,1-b]purin-4(3H)one;
cis-3-Cyclopentyl-5,6a,7,8,9,9a-Hexahydro-2,5-dimethyl-cyclopent[4,5]imidazo-[2,1-b]purin-4(3H)one;
5'-Methyl-2'-trifluoromethyl-3'-(phenylmethyl)spiro{cyclopentane-1,7'(8'H)-(3'H)imidazo[2,1-b]purin}-4-(5'H)-one;
7,8-Dihydro-5,7,7-trimethyl-2-trifluoromethyl-3-(phenylmethyl)-3H-imidazo[2,1-b]purin-4(5H)-one;
(+/−)-cis-5,6a,7,8,9,9a-Hexahydro-5-methyl-2-trifluoromethyl-3-(phenylmethyl)-cyclopent[4,5]imidazo[2,1-b]purin-4(3H)-one;
(+/−)-6a,7,8,9,9a,10,11,11a-Octahydro-2,5-dimethyl-3-(phenylmethyl)-3H-pentaleno[6a',1':4,5]imidazo[2,1-b]purin-4(5H)-one;
(+)-6a,7,8,9,9a,10,11,11a-Octahydro-2,5-dimethyl-3-phenylmethyl-3H-pentaleno[6a',1':4,5]imidazo[2,1-b]purin-4(5H)-one;
(−)-6a,7,8,9,9a,10,11,11a-Octahydro-2,5-dimethyl-3-phenylmethyl-3H-pentaleno[6a',1':4,5]Imidazo[2,1-b]purin-4(5H)-one;
(+/−) 6a,7,8,9,9a,10,11,11a-Octahydro-2,5-dimethyl-3H-pentaleno[6a',1':4,5]-imidazo[2,1-b]purin-4(5H)-one;
(+)-6a,7,8,9,9a,10,11,11a-Octahydro-2,5-dimethyl-3H-pentaleno[6a',1':4,5]-imidazo[2,1-b]purin-4(5H)-one;
(−)-6a,7,8,9,9a,10,11,11a-Octahydro-2,5-dimethyl-3H-pentaleno[6a',1':4,5]-imidazo[2,1-b]purin-4(5H)-one;
6a,7,8,9,10,10a,11,12,13,13a-Decahydro-2,5-dimethyl-(3-phenylmethyl)-napth[1,8a-d]imidazo[2,1-b]purin-4(5H)one;
7(R)-Cyclohexyl-7,8-dihydro-2,5-dimethyl-3-(phenylmethyl)-3H-imidazo[2,1-b]purin-4(3H)-one;
7(R)-Cyclohexyl-7,8-dihydro-2,5-dimethyl-3H-imidazo[2,1-b]purin-4(5H)-one;
7(S)-Cyclohexyl-7,8-dihydro-2,5-dimethyl-3-(phenylmethyl)-3H-imidazo[2,1-b]purin-4(3H)-one;
7(S)-Cyclohexyl-7,8-dihydro-2,5-dimethyl-3H-imidazo[2,1-b]purin-4(5H)-one;
5,6a(R),7,8,9,9a(S)-Hexahydro-2,5-dimethyl-[3-(trimethylacetoxy)methyl]-cyclopent[4,5]imidazo[2,1-b]purin-4(3H)-one;
5,6a(R),7,8,9,9a(S)-Hexahydro-2,5-dimethyl-3-(4-pyridylmethyl)cyclopent-[4,5]imidazo[2,1-b]purin-4(3H)-one;
5,6a(R),7,8,9,9a(S)-Hexahydro-2,5-dimethyl-3-[2-(4-morpholinyl)-ethyl]cyclopent[4,5]imidazo[2,1-b]purin-4(3H)-one;
5,6a(R),7,8,9,9a(S)-Hexahydro-2,5-dimethyl-3-[acetoxymethyl]cyclopent-[4,5]imidazo[2.1-b]purin-4(3H)-one;
5,6a,7,8,9,9a-Hexahydro-2,5,6a-trimethyl-3-(phenylmethyl)cyclopent-[4,5]imidazo[2,1-b]purin-4(3H)-one;
5,6a(R),7,8,9,9a(S)-Hexahydro-2,5,6a-trimethyl-3-(phenylmethyl)-cyclopent[4,5]imidazo[2,1-b]purin-4(3H)-one;
5,6a(S),7,8,9,9a(R)-Hexahydro-2,5,6a-trimethyl-3-(phenylmethyl)-cyclopent[4,5]imidazo[2,1-b]purin-4(3H)-one;
cis-6a,7,8,9,10,10a-Hexahydro-2,5,7-trimethyl-3-(phenylmethyl)-3H-benzimidazo[2,1-b]purin-4(5H)-one;
cis-5,6a,7,8,9,9a-Hexahydro-2,5,6a-trimethylcyclopent[4,5]imidazo[2,1-b]purin-4(3H)-one; or
cis-[6a,7,8,9,10,10a-Hexahydro-2,5,7-trimethyl-3H-benzimidazo[2,1-b]purin-4(5H)-one],
in free or salt form.

5.8: A compound which is a substituted imidazo[2,1-b]purin-4-one, in free or pharmaceutically acceptable salt form, e.g. a compound of Formula VIIIa, VIIIb or according to any of formulae 5.1-5.7, wherein the compound inhibits phosphodiesterase-mediated (e.g., PDE 1-mediated, especially PDE1B-mediated) hydrolysis of cGMP, e.g., with an $IC_{50}$ of less than 10 μM, preferably less than 100 nM in an immobilized-metal affinity particle reagent PDE assay, for example, as described in Example 1 below.

In another embodiment, the PDE 1 Inhibitors for use in the methods of treatment described herein are Compounds of Formula IXa or IXb

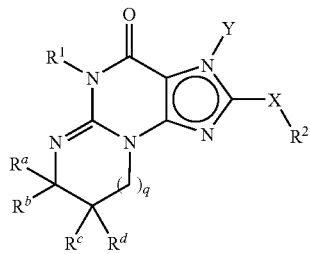

Formula IXa

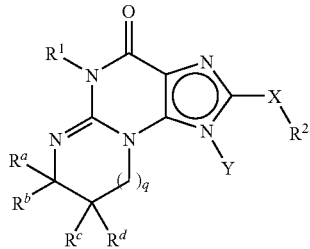

Formula IXb or a pharmaceutically acceptable salt thereof, wherein,
q=0 or 1;
$R^1$ is H, cycloalkyl, alkyl, $R^{23}$-alkyl- or $R^{26}$;
$R^a$, $R^b$ and $R^c$ are, independently of one another, each H, alkyl, cycloalkyl, aryl, $R^{22}$-aryl- or $R^{24}$-alkyl-; or
$R^a$ and $R^b$, together with the carbon to which they are both attached, form a 4- to 7-membered ring, and $R^c$ is H or alkyl; or
$R^a$ and $R^c$, together with the respective carbons to which they are attached, form a 4- to 7-membered ring, and $R^b$ is H or alkyl;
(i) X is a bond;
Y is aryl-alkyl or $R^{22}$-aryl-alkyl-; and
$R^2$ is monohaloalkyl, polyhaloalkyl, provided that it is not trifluoromethyl, azido, cyano, oximino, cycloalkenyl, heteroaryl, $R^{22}$-heteroaryl- or $R^{27}$-alkyl-;
(ii) X is a bond;
Y is aryl-alkyl or $R^{22}$-aryl-alkyl-; and
$R^2$ is H, halo, —$CONHR^6$, —$CONR^6R^7$, —$CO_2R^6$, monohaloalkyl, polyhaloalkyl, azido, cyano, —C═N—OR⁶, cycloalkyl, cycloalkylalkyl, R²⁶, aminosulfonyl, alkyl or R²³-alkyl- (iii) X is —O— or —S—;
Y is aryl-alkyl or R²²-aryl-alkyl-; and
R² is R²⁶, cycloalkyl cycloalkylalkyl, heterocycloalkyl, cycloalkenyl or R²⁶-alkyl-;

(iv) X is —O— or —S—;
Y is aryl-alkyl or R²²-aryl-alkyl-; and
R² is alkyl, R²⁶, cycloalkyl, cycloalkylalkyl, heterocycloalkyl, cycloalkenyl or R²⁸-alkyl-;

(v) X is —SO— or —SO₂—;
Y is aryl-alkyl or R²²-aryl-alkyl-; and
R² is alkyl, R²⁶, cycloalkyl, cycloalkylalkyl, heterocycloalkyl, cycloalkenyl or R²⁸-alkyl-;

(vi) X is —NR⁸—;
Y is aryl-alkyl or R²²-aryl-alkyl-; and
R² is (R²⁹)ₚ-alkyl-, cycloalkyl, (R³⁰)ₚ-cycloalkyl-, cycloalkenyl, (R³⁰)ₚ-cycloalkenyl-, heterocycloalkyl or (R³⁰)ₚ-heterocycloalkyl-:

(vii) X is —NR⁸—;
Y is aryl-alkyl or R²²-aryl-alkyl-; and
R² is alkyl, R²⁶, cycloalkyl, cycloalkylalkyl, heterocycloalkyl, cycloalkenyl or R³¹-alkyl-; or (viii) X is —C≡C—;
Y is aryl-alkyl or R²²-aryl-alkyl-; and
R² is alkyl, R²⁶, cycloalkyl, cycloalkylalkyl or R²³-alkyl-;

where,
R⁶ is H or R⁷;
R⁷ is alkyl, cycloalkyl or cycloalkylalkyl;
R⁸ is heterocycloalkyl or R⁶;
R²¹ is 1-6 substituents each independently selected from the group consisting of halo, hydroxy, alkoxy, phenoxy, phenyl, nitro, aminosulfonyl, cyano, monohaloalkyl, polyhaloalkyl, thiol, alkylthio, cycloalkyl, cycloalkylalkyl, amino, alkylamino, acylamino, carboxyl, —C(O)OR³⁴, carboxamido, —OCF₃ and acyloxy;
R²² is 1-6 substituents each independently selected from the group consisting of alkyl and R²¹;
R²³ is cycloalkoxy aryloxy, alkylthio, arylthio, cycloalkyl or R²⁸;
R²⁴ is cycloalkyl or R²⁶;
R²⁵ is hydroxy, alkoxy, amino, monoalkylamino, dialkylamino or R²⁶;
R²⁶ is aryl, R²²-aryl-, heteroaryl or R²²-heteroaryl-;
R²⁷ is cycloalkoxy, aryloxy, alkylthio, arylthio, heteroaryl, R²²-heteroaryl-, cycloalkyl, heterocycloalkyl, cycloalkenyl, cycloalkylamino or heterocycloalkylamino;
R²⁸ is cycloalkylamino, heterocycloalkylamino or R²⁵;
R²⁹ is alkoxy, cycloalkylamino, heterocycloalkylamino or R²⁶;
R³⁰ is halo, hydroxy, alkoxy, amino, aminosulfonyl, cyano, monohaloalkyl, polyhaloalkyl, thiol, alkylthio, alkyl, cycloalkyl, cycloalkylalkyl or acyloxy;
R³¹ is cycloalkyl or R²⁸;
R³⁴ is alkyl, aryl, aralkyl and heteroaryl; and
p is 1 to 4.

The invention further provides the use of PDE 1 Inhibitors of Formula IXa or IXb as follows:

6.1 Formula IXa or IXb selected from a group consisting of:

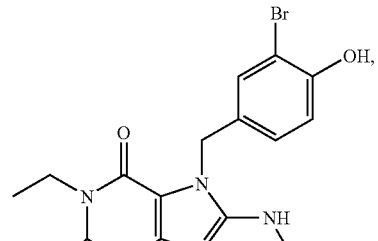

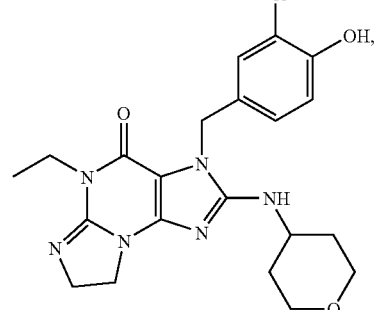

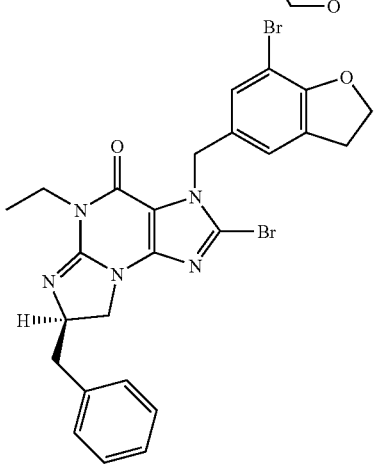

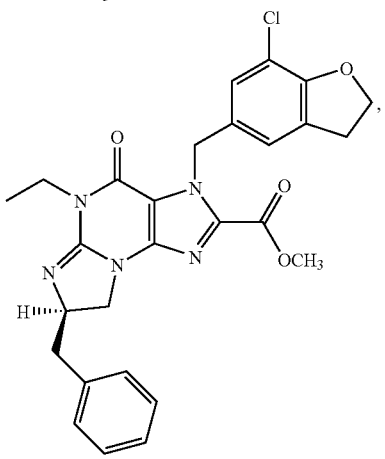

25
-continued
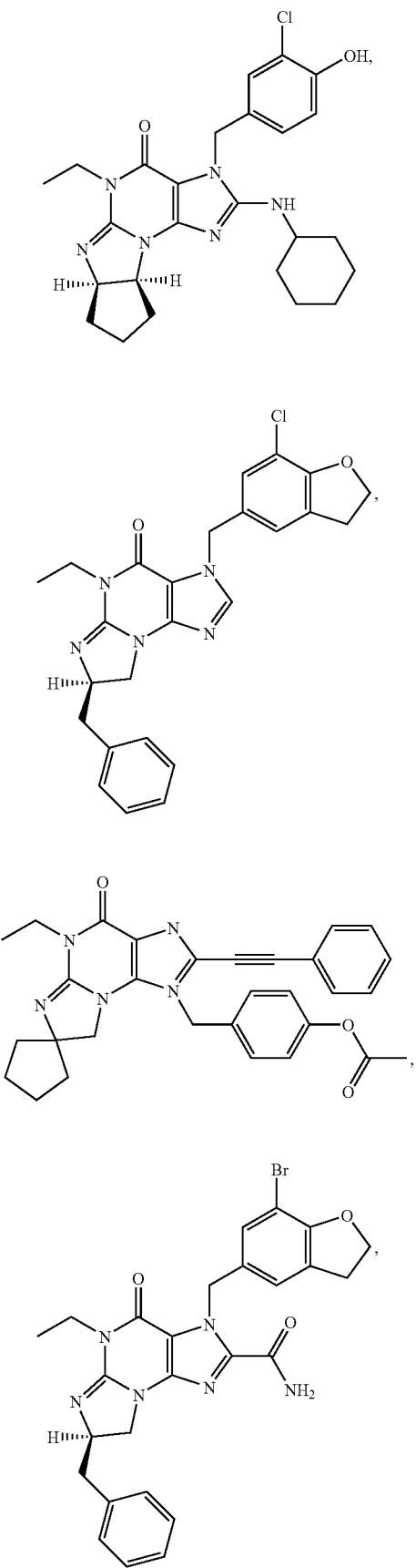
26
-continued
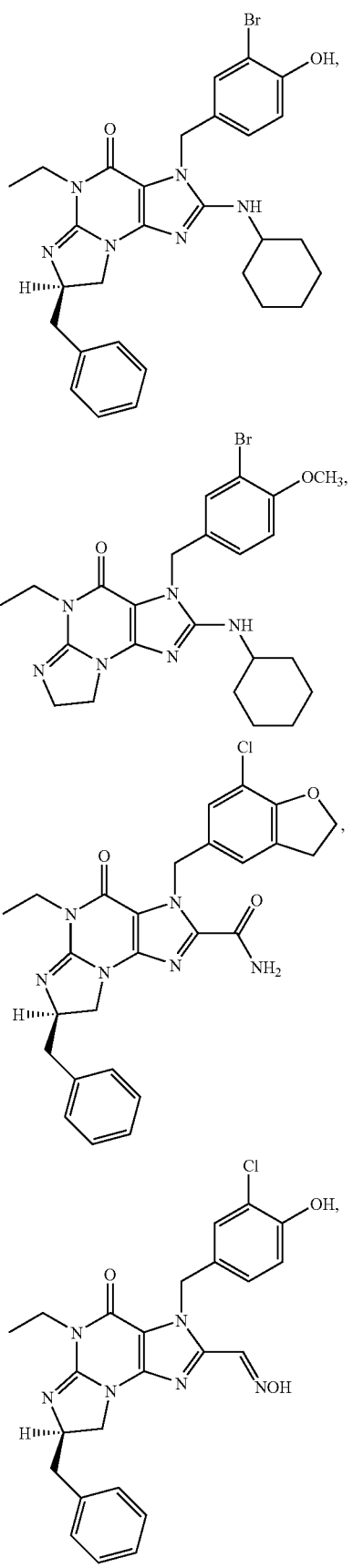

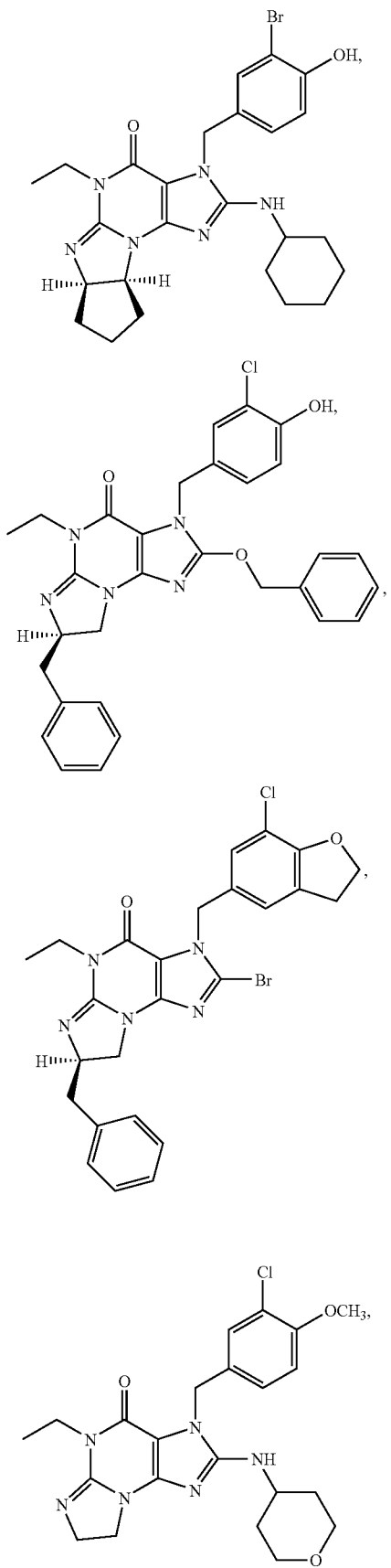
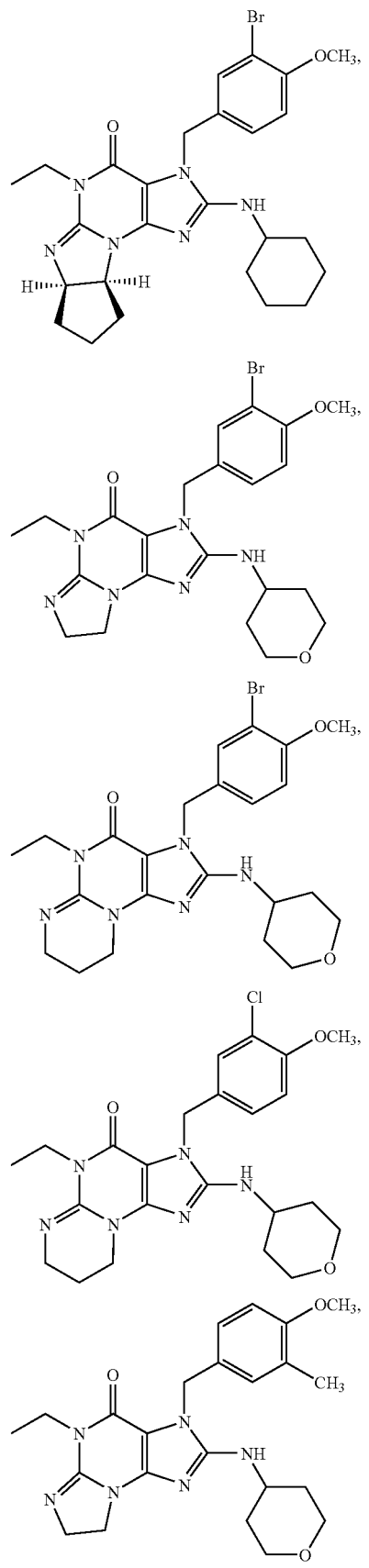

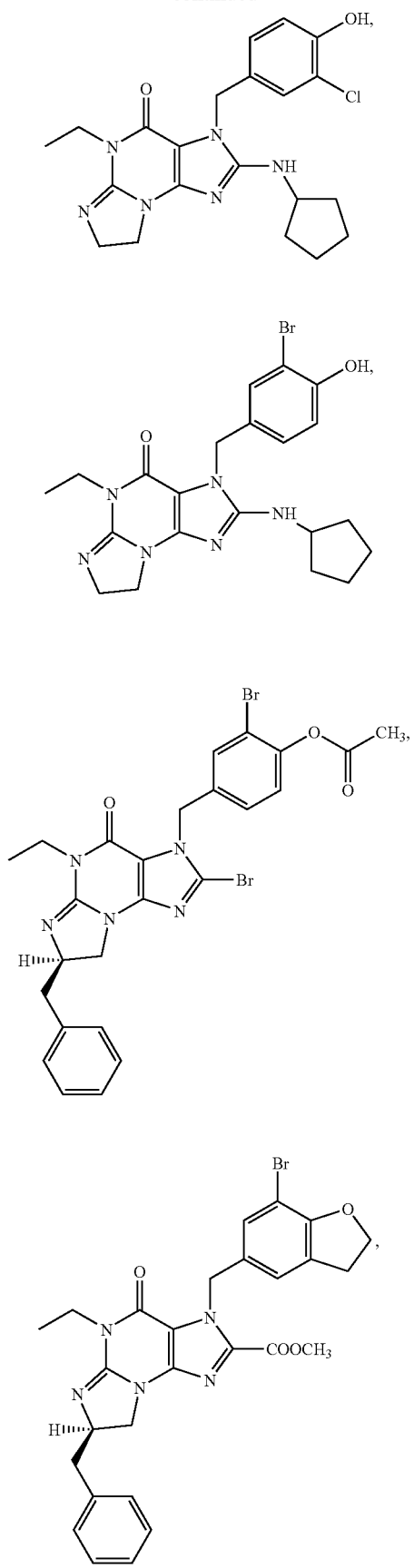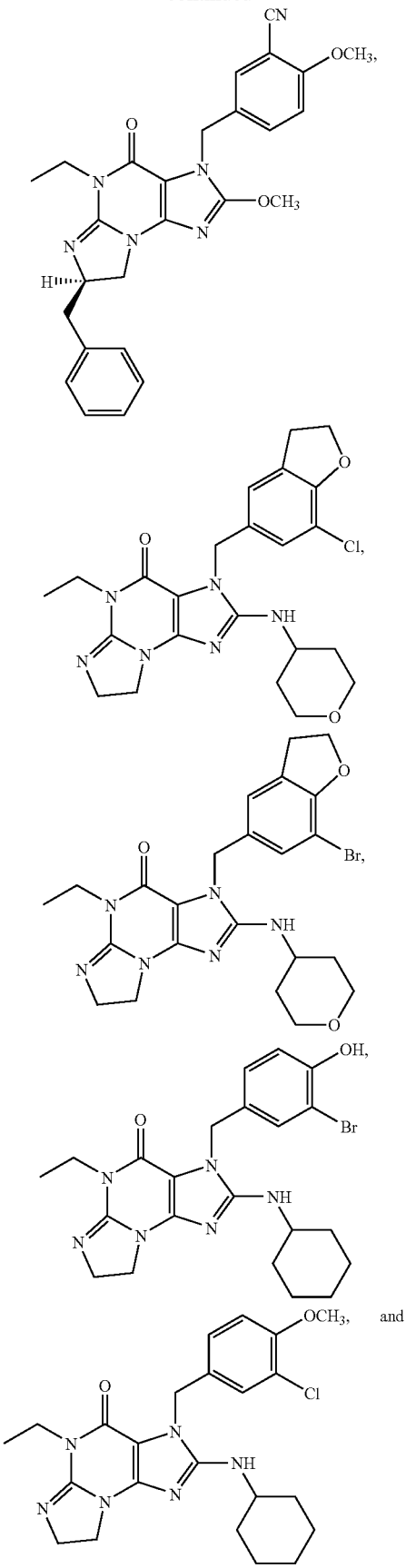

-continued
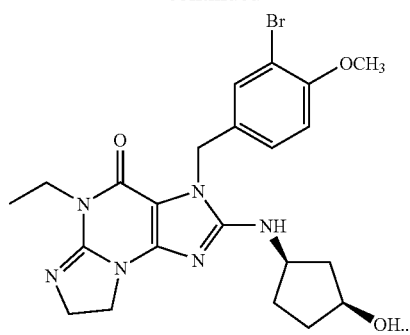 [SMILES: CCN1C(=O)c2c(nc(N[C@@H]3CC[C@H](O)C3)n2Cc2ccc(OC)c(Br)c2)N2CCN=C12]
6.2 Formula IXa or IXb, in free or salt form, selected from a group consisting of:
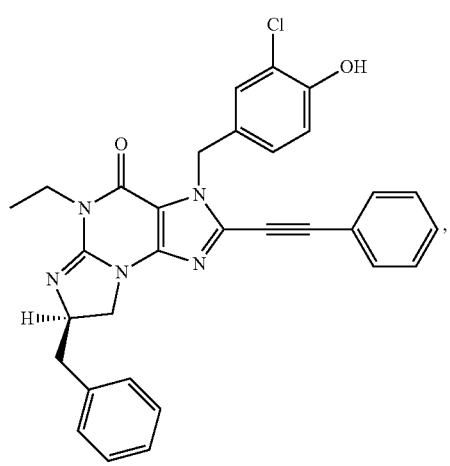
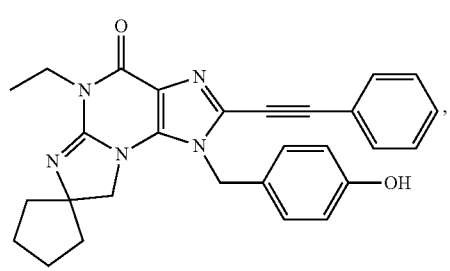
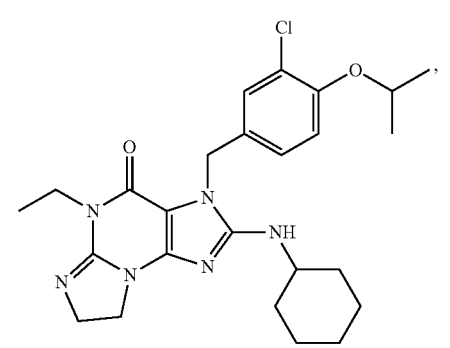
-continued
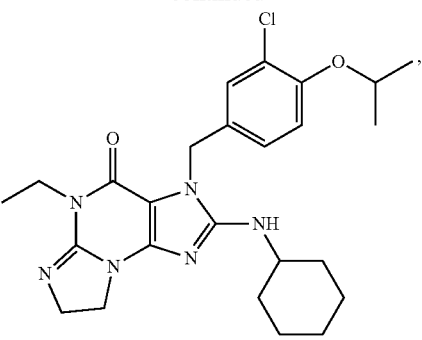
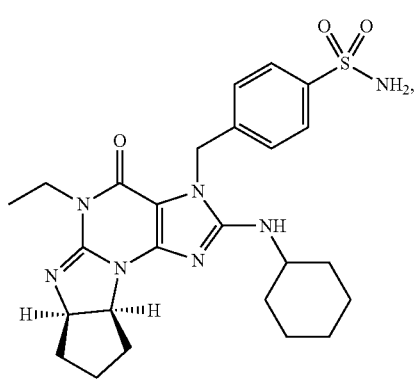
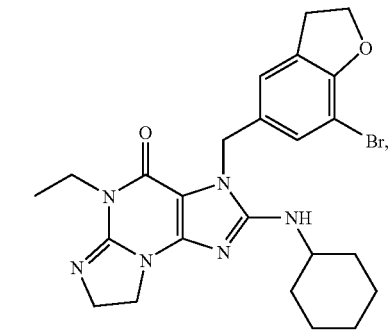
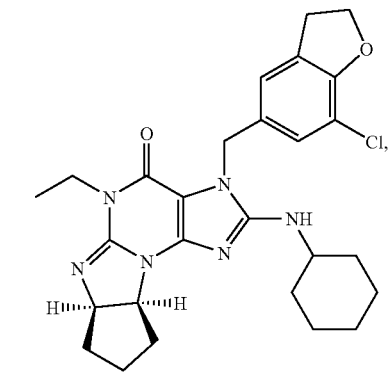

33
-continued
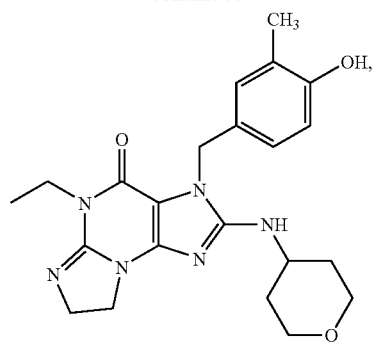
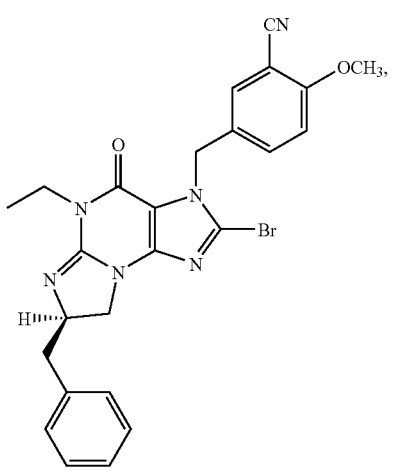
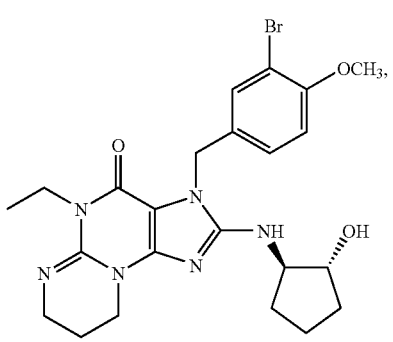
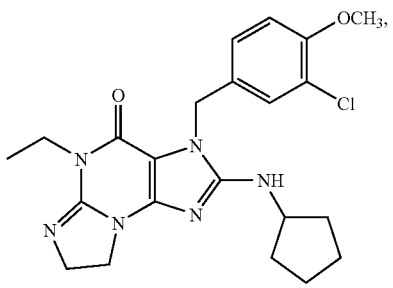
34
-continued
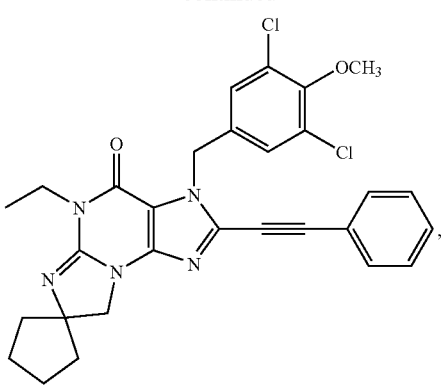
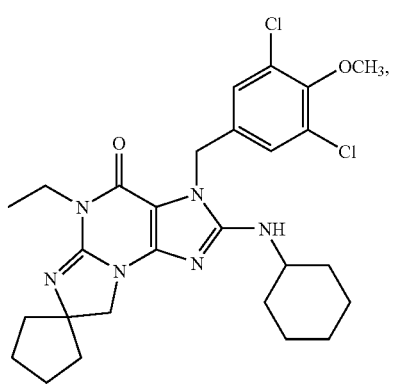
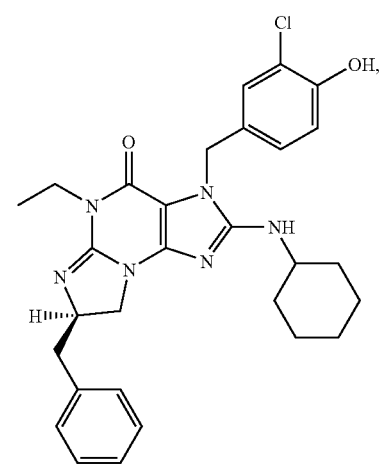
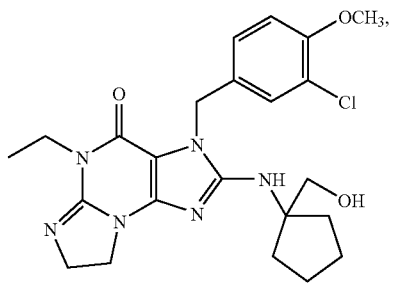

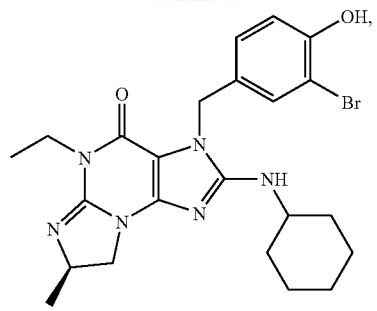
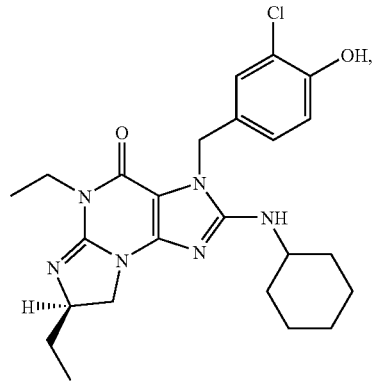
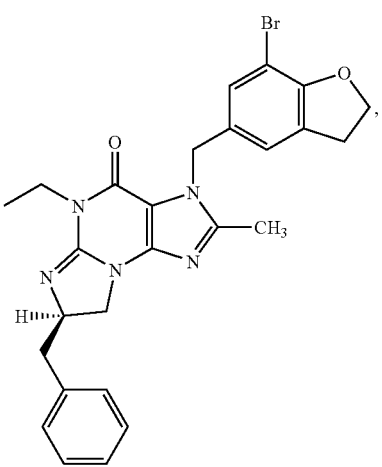
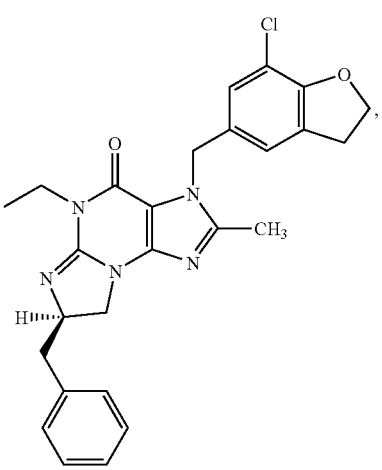
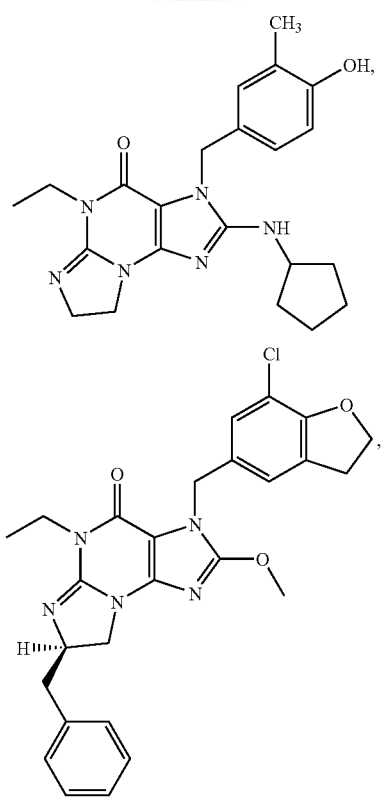
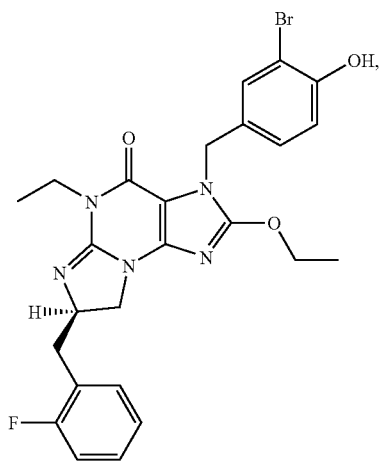
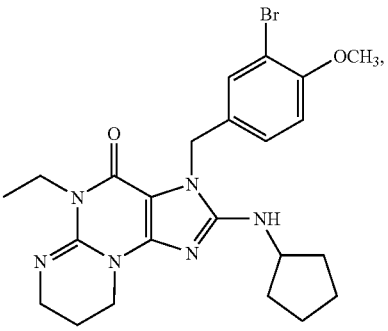

37
-continued

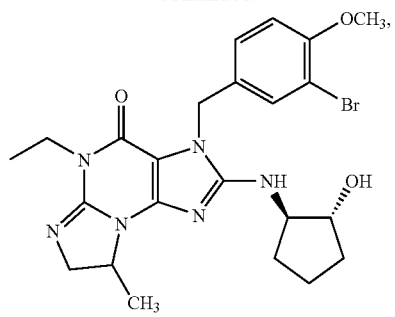

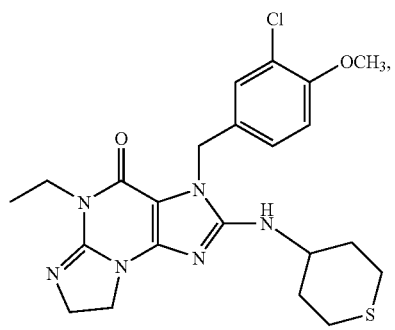

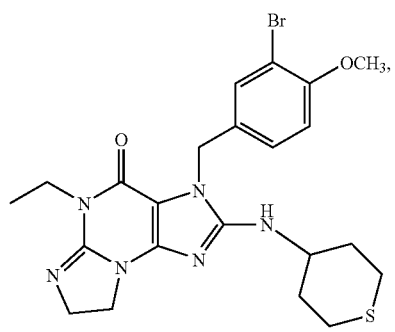

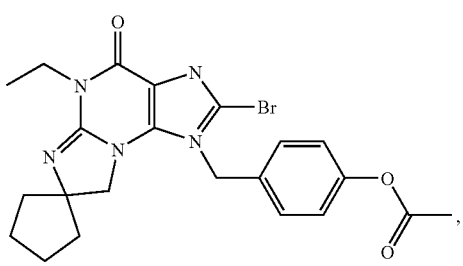

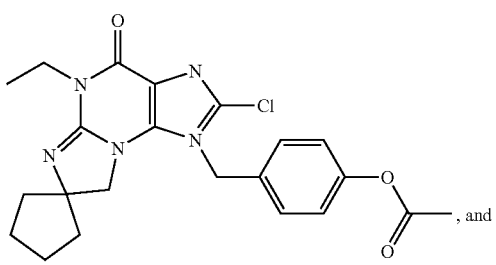

38
-continued

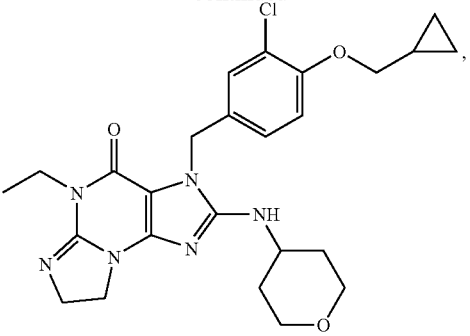

in free or salt form.

In another embodiment, the invention provides the use of PDE 1 Inhibitors of Formula X:

Formula X

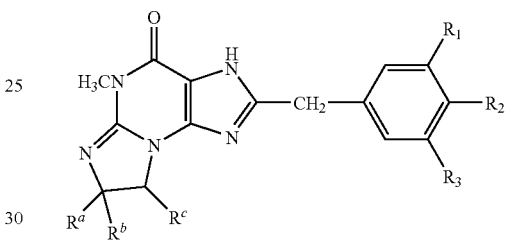

in free or a pharmaceutically acceptable salt thereof, wherein: $R_1$, $R_2$ and $R_3$ are independently selected from the group consisting of hydrogen, lower alkyl, lower alkoxy, halogeno, hydroxy, (di-lower alkyl)amino, 4-morpholinyl, 1-pyrrolidinyl, 1-pyrrolyl, —$CF_3$, —$OCF_3$, phenyl and methoxyphenyl; or $R_1$ and $R_2$ together are methylenedioxy; or $R_1$ and $R_2$ together with the carbon atoms to which they are attached form a benzene ring; and $R^a$ is hydrogen and $R^b$ and $R^c$, together with the carbon atoms to which they are attached, form a saturated ring of 5 carbons; or $R^a$ is lower alkyl, $R^b$ is hydrogen or lower alkyl, and $R^c$ is hydrogen; or $R^a$, $R^b$ and the carbon atom to which they are attached form a saturated ring of 5-7 carbons, and $R^c$ is hydrogen; or $R^a$ is hydrogen, and $R^b$, $R^c$ and the carbon atoms to which they are attached form a tetrahydrofuran ring; or $R^a$ and $R^b$, together with the carbon atom to which they are attached, and $R^b$ and $R^c$, together with the carbon atoms to which they are attached, each form a saturated ring of 5-7 carbons.

In a further embodiment, the invention provides the use of PDE 1 Inhibitors of Formula X as follows:

7.1 Formula X, wherein $R_1$, $R_2$ and $R_3$ are independently selected from the group consisting of hydrogen, lower alkyl, lower alkoxy, halogeno, hydroxy, (di-lower alkyl) amino, 4-morpholinyl, 1-pyrrolidinyl, 1-pyrrolyl, —$CF_3$, —$OCF_3$, phenyl and methoxyphenyl; or $R_1$ and $R_2$ together are methylenedioxy; or $R_1$ and $R_2$ together with the carbon atoms to which they are attached form a benzene ring;

7.2 Formula X or 7.1, wherein $R_1$ is H, methoxy or trifluoromethyl;

7.3 Formula X or 7.1 or 7.2, wherein $R_1$ is H, 7.4 Formula X or any of 7.1-7.3, wherein $R_2$ is selected from a group consisting of H, halo (e.g., F, Cl), methoxy, methyl, trifluoromethyl, dimethylamino, phenyl, methoxyphenyl-, —OCF₃, 3,4-OCH₂O—, pyrrolidin-1-yl, pyrol-1-yl and morpholin-4-yl;

7.5 Formula X or any of 7.1-7.4, wherein $R_1$ and $R_2$ together with the carbon atoms to which they are attached form a benzene ring;

7.6 Formula X or any of 7.1-7.5, wherein $R_3$ is H or methoxy;

7.7 Formula X or any of 7.1-7.6, wherein $R_3$ is H;

7.8 Formula X or any of 7.1-7.7, wherein $R^a$ is hydrogen and $R^b$ and $R^c$, together with the carbon atoms to which they are attached, form a saturated ring of 5 carbons; or $R^a$ is lower alkyl, $R^b$ is hydrogen or lower alkyl, and $R^c$ is hydrogen; or $R^a$, $R^b$ and the carbon atom to which they are attached form a saturated ring of 5-7 carbons, and $R^c$ is hydrogen; or $R^a$ is hydrogen, and $R^b$, $R^c$ and the carbon atoms to which they are attached form a tetrahydrofuran ring; or $R^a$ and $R^b$, together with the carbon atom to which they are attached, and $R^b$ and $R^c$, together with the carbon atoms to which they are attached, each form a saturated ring of 5-7 carbons;

7.9 Formula X or any of 7.1-7.8, wherein $R^a$ is hydrogen and $R^b$ and $R^c$ together with the carbon atoms to which they are attached, form a saturated ring of 5 carbons, and wherein $R_1$, $R_2$ and $R_3$ are as defined in the following table

| $R_1$ | $R_2$ | $R_3$ |
|---|---|---|
| H | H | H |
| —OCH₃ | H | H |
| H | F | H |
| H | —OCH₃ | H |
| H | OH | H |
| H | —CH₃ | H |
| H | (CH₃)₂N— | H |
| —OCH₃ | —OCH₃ | —OCH₃ |
| —OCH₃ | —OCH₃ | H |
| —CF₃ | H | H |
| H | C₆H₅— | H |
| H | —OCF₃ | H |
| H | —N(pyrrolidinyl) | H |
| H | —N(pyrrolyl) | H |
| | 3,4-OCH₂O— | H |
| H | —N(morpholinyl) | H |
| H | —C₆H₄—OCH₃ | H |
| $R_1$ and $R_2$, together with the carbon atoms to which they are attached form a benzene ring | | H |
| H | Cl | H. |

7.10 Formula X or any of 7.1-7.9, selected from a group consisting of

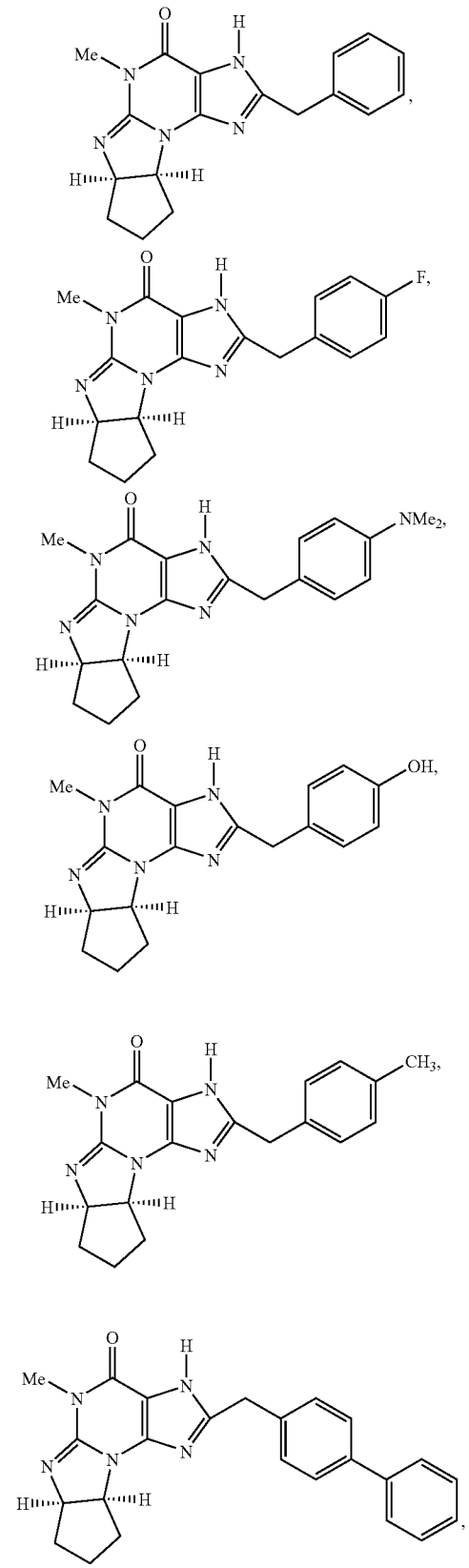

-continued

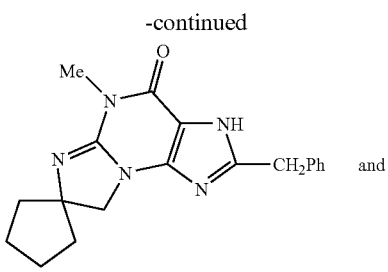 and

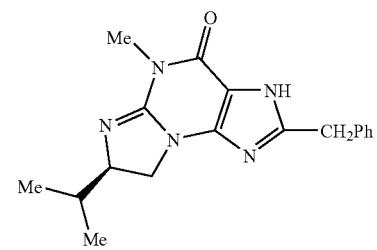

7.11 Formula X or any of 7.1-7.9, selected from a group consisting of:

2'-benzyl-5'-methyl-spiro[cyclopentane-1',7'(8'H)-[3'H]-imidazo[2,1-b]purin]-4'-(5'H)-one;

2'-benzyl-5,7,7-trimethyl-3H-imidazo[2,1-b]purin-4-(5H)-one;

(+)-2-benzyl-7,8-dihydro-5-methyl-7-(1-methylethyl)-1H-imidazo[2,1-b]-purin-4(5H)-one;

(+,−)-6a,7,8,9,9a,10,11,11a-octahydro-5-methyl-2-(3,4-methylene-dioxyphenylmethyl)-3H-pentalen[6a,1:4,5]imidazo[2,1-b]purin-4(5H)-one; and (+)-cis-6a,7,9,9a-tetrahydro-5-methyl-2-[4-(trifluoromethyl)-phenylmethyl]-3H-furo[3',4':4,5]imidazo[2,1-b]purin-4(5H)-one, in free or salt form.

7.12 Formulae X or 7.1-7.11, wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 1;

In another embodiment, the invention provides the use of PDE 1 Inhibitors selected from the following:

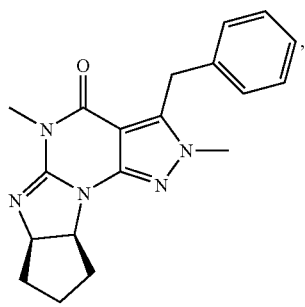

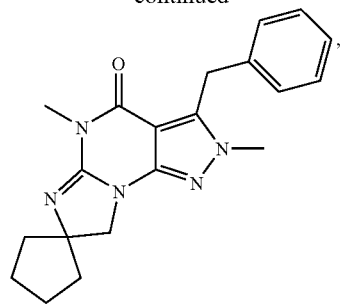

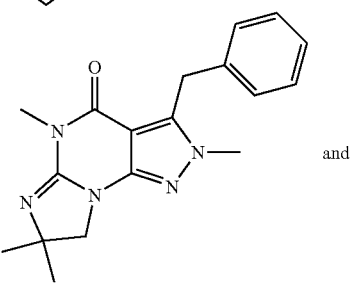 and

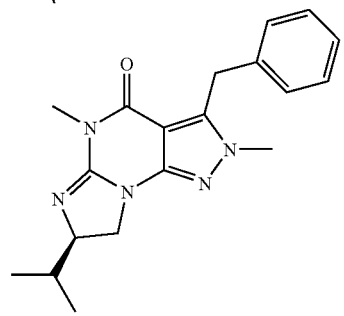

in free or salt form (Formula XI).

If not otherwise specified or clear from context, the following terms as used herein have the following meanings:

a. "Alkyl" as used herein is a saturated or unsaturated hydrocarbon moiety, preferably saturated, preferably one to seven carbon atoms in length, which may be linear or branched, and may be optionally substituted, e.g., mono-, di-, or tri-substituted, e.g., with halogen (e.g., chloro or fluoro), hydroxy, or carboxy.

b. "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy.

c. "Heterocycloalkyl" as used herein is a saturated or unsaturated nonaromatic hydrocarbon moiety, preferably saturated, preferably comprising three to nine carbon atoms, at least one atom selected from a group consisting of N, O or S, at least some of which form a nonaromatic mono- or bicyclic, or bridged cyclic structure, and which may be optionally substituted, e.g., with halogen (e.g., chloro or fluoro), hydroxy, or carboxy. Examples of heterocycloalkyl include pyrrolidinyl (e.g., pyrrolidin-1-yl), morpholinyl (e.g., morpholin-4-yl), d. "Aryl" as used herein is a mono or bicyclic aromatic hydrocarbon (e.g., phenyl, naphthyl), preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

e. "Heteroaryl" as used herein is an aromatic moiety wherein one or more of the atoms making up the aromatic ring is sulfur or nitrogen rather than carbon, e.g., pyridyl, thiadiazolyl, pyrrolyl (e.g., pyrrol-2-yl) or imidazolyl (e.g., 1H-imidazol-2-yl), which may be optionally substituted, e.g., with alkyl, halogen, haloalkyl, hydroxy or carboxy.

PDE 1 Inhibitors may exist in free or salt form, e.g., as acid addition salts. In this specification unless otherwise indicated language such as PDE 1 Inhibitors is to be understood as embracing the compounds in any form, for example free or acid addition salt form, or where the compounds contain acidic substituents, in base addition salt form. The PDE 1 Inhibitors are intended for use as pharmaceuticals, therefore pharmaceutically acceptable salts are preferred. Salts which are unsuitable for pharmaceutical uses may be useful, for example, for the isolation or purification of free PDE 1 Inhibitors or their pharmaceutically acceptable salts.

PDE 1 Inhibitors may in some cases also exist in prodrug form, for example when the compounds contain physiologically hydrolysable and acceptable esters. As used herein, "physiologically hydrolysable and acceptable ester" means esters of PDE 1 Inhibitors which are hydrolysable under physiological conditions to yield acids (in the case of PDE 1 Inhibitors which have hydroxy substituents) or alcohols (in the case of PDE 1 Inhibitors which have carboxy substituents) which are themselves physiologically tolerable at doses to be administered. As will be appreciated the term thus embraces conventional pharmaceutical prodrug forms.

Methods of making and formulating the PDE 1 Inhibitors, novel intermediates useful for making PDE 1 Inhibitors, and methods of using the PDE 1 Inhibitors for treatment of diseases are generally disclosed in EP 0201188 (or U.S. Pat. No. 4,666,908) and EP 0911333 (or U.S. Pat. No. 6,235,742); PCT/US2006/022066; PCT/US2006/033179; WO 03/042216 (U.S. Pat. No. 6,943,171); U.S. Pat. No. 6,969,719; U.S. Pat. No. 5,939,419; EP 0 538 332 (U.S. Pat. No. 5,393,755); U.S. Pat. No. 5,393,755; U.S. Pat. No. 6,969,719 B2, Xia et al., *J. Med. Chem.* (1997), 40, 4372-4377 and Ahn et al., *J. Med. Chem.* (1997), 40, 2196-2210, the contents of all of which are incorporated herein by reference.

Methods of Treatment

The invention provides methods of treatment or prophylaxis of narcolepsy comprising administering an effective amount of a PDE 1 inhibitor, e.g., a PDE 1 Inhibitor as hereinbefore described, for example a Compound of any of Formulae I, Ia, II, III, IV, V, VI, VIIa, VIIb, VIIIa, VIIIb, IXa, IXb, X, XI or any of Formulae 1.2-1.17, 2.1-2.9, or 3.2-3.22, 4.1-4.17, 5.1-5.8, 6.1-6.1 or 7.1-7.12 to a human or animal patient, preferably a human, in need thereof.

PDE 1 Inhibitors may be used in the foregoing methods of treatment prophylaxis as a sole therapeutic agent, but may also be used in combination or for co-administration with other active agents. Thus, the invention further comprises a method of treating narcolepsy comprising administering simultaneously, sequentially, or contemporaneously administering therapeutically effective amounts of (i) a PDE 1 Inhibitor, e.g., any of Formulae I, Ia, II, III, IV, V, VI, VIIa, VIIb, VIIIa, VIIIb, IXa, IXb, X, XI or any of Formulae 1.2-1.17, 2.1-2.9, 3.2-3.22, 4.1-4.17, 5.1-5.8, 6.1-6.2 or 7.1-7.12; and (ii) a compound to promote wakefulness or regulate sleep, e.g., selected from (a) central nervous system stimulants-amphetamines and amphetamine like compounds, e.g., methylphenidate, dextroamphetamine, methamphetamine, and pemoline; (b) modafinil, (c) antidepressants, e.g., tricyclics (including imipramine, desipramine, clomipramine, and protriptyline) and selective serotonin reuptake inhibitors (including fluoxetine and sertraline); and/or (d) gamma hydroxybutyrate (GHB), to a patient in need thereof.

The present invention also provides (i) a PDE 1 Inhibitor for use in the treatment of any disease or condition as hereinbefore set forth, or in a method of treatment as hereinbefore set forth;

(ii) the use of a PDE 1 Inhibitor in the manufacture of a medicament for treating a disease or condition as hereinbefore set forth, or manufacture of a medicament for use in a method of treatment as hereinbefore set forth; and (iii) a pharmaceutical composition comprising a PDE 1 Inhibitor in combination or association with a pharmaceutically acceptable diluent or carrier for use in the treatment of a disease or condition as hereinbefore set forth, or for use in a method of treatment as hereinbefore set forth.

The words "treatment" and "treating" are to be understood accordingly as embracing prophylaxis and treatment or amelioration of any of the symptoms of disease as well as treatment of the cause of the disease.

Dosages employed in practicing the present invention will of course vary depending, e.g. on the particular disease or condition to be treated, the particular PDE 1 Inhibitor used, the mode of administration, and the therapy desired. PDE 1 Inhibitors may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a PDE 1 Inhibitor, together with a pharmaceutically acceptable diluent or carrier therefor.

Pharmaceutical compositions comprising PDE 1 Inhibitors may be prepared using conventional diluents or excipients and techniques known in the galenic art. Thus oral dosage forms may include tablets, capsules, solutions, suspensions and the like.

EXAMPLES

1. Measurement of PDE1B Inhibition In Vitro Using IMAP Phosphodiesterase Assay Kit Phosphodiesterase 1B (PDE1B) is a calcium/calmodulin dependent phosphodiesterase enzyme that converts cyclic guanosine monophosphate (cGMP) to 5'-guanosine monophosphate (5'-GMP). PDE1B can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein-IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Δmp). Inhibition of phosphodiesterase, therefore, is detected as a decrease in Δmp.

Enzyme Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: 3',5'-cyclic-nucleotide-specific bovine brain phosphodiesterase (Sigma, St. Louis, Mo.) is reconstituted with 50% glycerol to 2.5 U/ml. One unit of enzyme will hydrolyze 1.0 μmole of 3',5'-cAMP to 5'-AMP per min at pH 7.5 at 30° C. One part enzyme is added to 1999 parts reaction buffer (30 μM $CaCl_2$, 10 U/ml of calmodulin (Sigma P2277), 10 mM Tris-HCl pH 7.2, 10 mM $MgCl_2$, 0.1% BSA, 0.05% $NaN_3$) to yield a final concentration of 1.25 mU/ml. 99 μl of diluted enzyme solution is added into each well in a flat bottom 96-well polystyrene plate to which 1 μl of test compound dissolved in 100% DMSO is added. The compounds are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Δmp).

A decrease in GMP concentration, measured as decreased Δmp, is indicative of inhibition of PDE activity. $IC_{50}$ values are determined by measuring enzyme activity in the presence of 8 to 16 concentrations of compound ranging from 0.0037 nM to 80,000 nM and then plotting drug concentration versus ΔmP, which allows $IC_{50}$ values to be estimated using nonlinear regression software (XLFit; IDBS, Cambridge, Mass.).

What is claimed is:

1. A method of treatment for narcolepsy comprising administering an effective amount of a PDE 1 inhibitor to a patient in need thereof wherein the PDE 1 inhibitor is a compound of the formula (I):

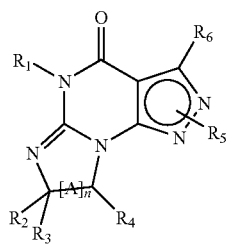

Formula I wherein
(i) $R_1$ is H or $C_{1-4}$ alkyl;
(ii) $R_4$ is H or $C_{1-4}$ alkyl and $R_2$ and $R_3$ are, independently, H or $C_{1-4}$ alkyl, aryl, heteroaryl, heteroarylalkoxy, arylalkoxy, heteroarylalkyl, or arylalkyl;
or $R_2$ is H and $R_3$ and $R_4$ together form a di-, tri-, or tetra-methylene bridge;
(iii) $R_5$ is a substituted heteroarylalkyl, or $R_5$ is attached to one of the nitrogen atoms on the pyrazolo portion of Formula I and is a moiety of Formula Q

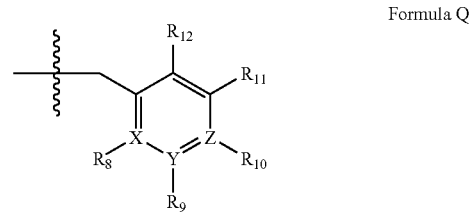

Formula Q wherein X, Y and Z are, independently, N or C; $R_8$, $R_9$, $R_{11}$ and $R_{12}$ are independently H or halogen; and $R_{10}$ is halogen, alkyl, cycloalkyl, haloalkyl, aryl, heteroaryl, or thiadiazolyl, diazolyl, triazolyl, tetrazolyl, arylcarbonyl, alkylsulfonyl, heteroarylcarbonyl, or alkoxycarbonyl; provided that when X, Y, or Z is nitrogen, $R_8$, $R_9$, or $R_{10}$, respectively, is not present;
(iv) $R_6$ is phenylamino or benzylamino; and
(v) n=0;
wherein:
said aryl is optionally substituted with alkyl, halogen, haloalkyl, hydroxy, carboxy or an additional aryl or heteroaryl; and
said heteroaryl is optionally substituted with alkyl, halogen, haloalkyl, hydroxy or carboxy,
in free, pharmaceutically acceptable salt or prodrug form.

2. The method according to claim 1 wherein the PDE 1 inhibitor is a compound of Formula III:

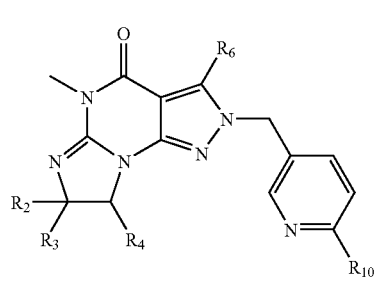

Formula III wherein
$R_2$ is H and $R_3$ and $R_4$ together form a tri- or tetramethylene bridge; or at least one of $R_2$ and $R_3$ is methyl, isopropyl or arylalkoxy and $R_4$ is H; or $R_2$ and $R_3$ are H and $R_4$ is a $C_{1-4}$ alkyl;
$R_6$ is phenylamino or benzylamino;
$R_{10}$ is haloalkyl, phenyl, pyridyl, or thiadiazolyl;
wherein:
said phenyl is optionally substituted with alkyl, halogen, haloalkyl, hydroxy, carboxy or an additional aryl or heteroaryl; and
said pyridyl and thiadiazolyl are optionally substituted with alkyl, halogen, haloalkyl, hydroxy or carboxy,
in free or pharmaceutically acceptable salt form.

3. The method according to claim 1 wherein the PDE 1 inhibitor is a compound of Formula IV:

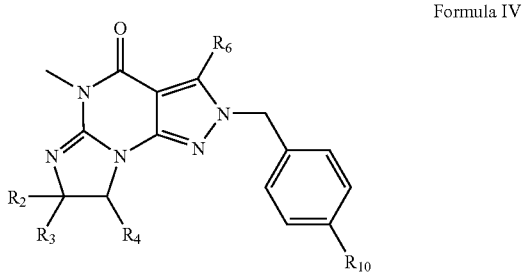

Formula IV wherein
$R_2$ is H and $R_3$ and $R_4$ together form a tri- or tetra-methylene bridge; or at least one of $R_2$ and $R_3$ is methyl, isopropyl or arylalkoxy and $R_4$ is H; or $R_2$ and $R_3$ are H and $R_4$ is a $C_{1-4}$ alkyl;
$R_6$ is phenylamino or benzylamino;
$R_{10}$ is phenyl, pyridyl, or thiadiazolyl;
wherein:
said phenyl is optionally substituted with alkyl, halogen, haloalkyl, hydroxy, carboxy or an additional aryl or heteroaryl; and
said pyridyl and thiadiazolyl are optionally substituted with alkyl, halogen, haloalkyl, hydroxy or carboxy,
in free or pharmaceutically acceptable salt form.

4. The method according to claim 1 wherein the PDE 1 inhibitor is a compound of formula Ia:

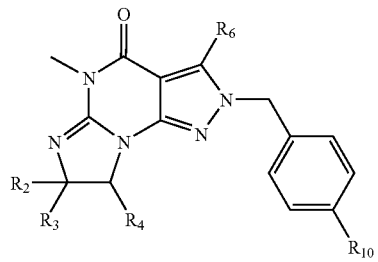

Formula Ia wherein
(i) $R_1$ is H or $C_{1-4}$ alkyl;
(ii) $R_4$ is H and $R_2$ and $R_3$ are, independently, H or $C_{1-4}$ alkyl, aryl, or arylalkyl;
or $R_2$ is H and $R_3$ and $R_4$ together form a di-, tri- or tetramethylene bridge;
(iii) $R_5$ is attached to one of the nitrogens on the pyrazolo portion of formula I and is a substituted benzyl of formula Qa

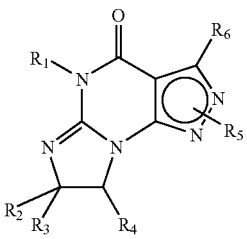

Formula Qa wherein $R_8$, $R_9$, $R_{11}$ and $R_{12}$ are independently H or halogen; and $R_{10}$ is halogen, alkyl, cycloalkyl, haloalkyl, aryl, heteroaryl, arylcarbonyl, alkyl sulfonyl or heteroarylcarbonyl, and (iv) $R_6$ is phenylamino or benzylamino
wherein:
said aryl is optionally substituted with alkyl, halogen, haloalkyl, hydroxy, carboxy or an additional aryl or heteroaryl; and
said heteroaryl is optionally substituted with alkyl, halogen, haloalkyl, hydroxy or carboxy,
in free, pharmaceutically acceptable salt or prodrug form.

5. The method according to claim 1 wherein the PDE 1 inhibitor is a compound of Formula V:

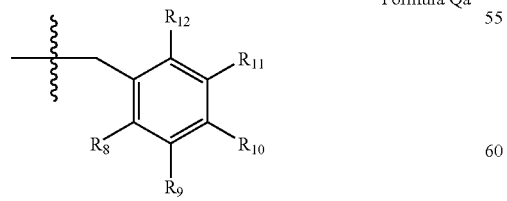

Formula V wherein
$R_2$ is H and $R_3$ and $R_4$ together form a tri- or tetra-methylene bridge; or $R_2$ and $R_3$ are each methyl and $R_4$ is H; or $R_2$ and $R_4$ are H and $R_3$ is isopropyl;
$R_6$ is phenylamino or benzylamino;
$R_{10}$ is phenyl, pyridyl, or thiadiazolyl;
wherein:
said phenyl is optionally substituted with alkyl, halogen, haloalkyl, hydroxy, carboxy or an additional aryl or heteroaryl; and
said pyridyl and thiadiazolyl are optionally substituted with alkyl, halogen, haloalkyl, hydroxy or carboxy,
in free or pharmaceutically acceptable salt form.

6. The method according to claim 1, wherein the PDE 1 inhibitor inhibits phosphodiesterase-mediated hydrolysis of cGMP or cAMP.

7. The method according to claim 1, wherein the PDE1 inhibitor is a PDE1B inhibitor.

8. The method according claim 1 further comprising administering a compound or compounds selected from central nervous system stimulants, modafinil, antidepressants, and gamma hydroxybutyrate.

9. The method according to claim 1 wherein the PDE 1 inhibitor is:

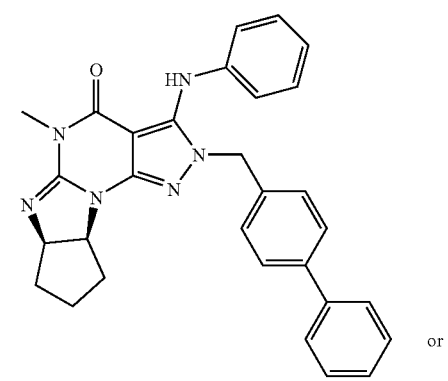

or

-continued

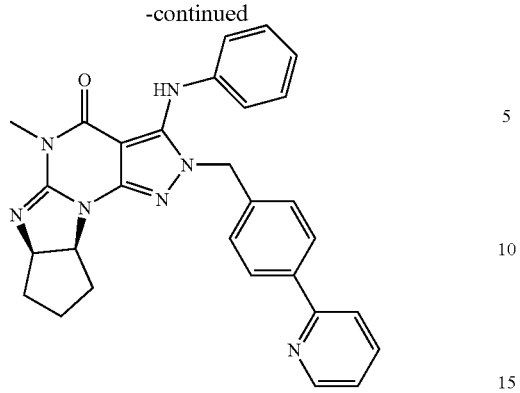

in free or pharmaceutically acceptable salt form.

10. The method according to claim 1, wherein $R_{10}$ is:
aryl wherein said aryl is substituted with alkyl, halogen, haloalkyl, hydroxy, carboxy or an additional aryl or heteroaryl; or
heteroaryl where said heteroaryl is substituted with alkyl, halogen, haloalkyl, hydroxy or carboxy.

11. The method according to claim 1, wherein $R_6$ is:
phenylamino wherein said phenyl is substituted with alkyl, halogen, haloalkyl, hydroxy, carboxy or an additional aryl or heteroaryl.

12. The method according to claim 5, wherein $R_{10}$ is pyridyl substituted with alkyl, halogen, haloalkyl, hydroxy or carboxy.

* * * * *